US011773496B2

(12) United States Patent
Schwenk et al.

(10) Patent No.: US 11,773,496 B2
(45) Date of Patent: Oct. 3, 2023

(54) COMBINED ELECTRICAL LEAD AND GAS PORT TERMINALS AND ELECTROLYTIC GAS GENERATOR COMPRISING SAME

(71) Applicant: Giner Life Sciences, Inc., Newton, MA (US)

(72) Inventors: Melissa N. Schwenk, Waltham, MA (US); Simon G. Stone, Arlington, MA (US)

(73) Assignee: GINER, INC., Newton, MA (US)

(*) Notice: Subject to any disclaimer, the term of this patent is extended or adjusted under 35 U.S.C. 154(b) by 227 days.

(21) Appl. No.: 16/415,977

(22) Filed: May 17, 2019

(65) Prior Publication Data

US 2019/0368056 A1    Dec. 5, 2019

Related U.S. Application Data

(60) Provisional application No. 62/672,784, filed on May 17, 2018.

(51) Int. Cl.
*C25B 1/01* (2021.01)
*C25B 1/04* (2021.01)
(Continued)

(52) U.S. Cl.
CPC .......... *C25B 1/04* (2013.01); *A61M 5/14276* (2013.01); *C25B 9/73* (2021.01);
(Continued)

(58) Field of Classification Search
CPC .... C25B 9/65; C25B 9/73; C25B 1/04; C25B 13/02; A61M 2202/0208; A61M 2005/14204; A61M 2005/006; A61M 5/14276; Y02E 60/36
See application file for complete search history.

(56) References Cited

U.S. PATENT DOCUMENTS

| 150,995 A | 5/1874 | Zwietusch |
|---|---|---|
| 3,005,943 A | 10/1961 | Jaffe |

(Continued)

FOREIGN PATENT DOCUMENTS

| CA | 2112952 A1 | 6/1995 |
|---|---|---|
| CN | 1036511 A | 10/1989 |

(Continued)

OTHER PUBLICATIONS

International Search Report dated Aug. 6, 2019, from PCT Application No. PCT/US2019/032990, the corresponding PCT application to the present application.

(Continued)

*Primary Examiner* — Zulmariam Mendez
(74) *Attorney, Agent, or Firm* — KRIEGSMAN & KRIEGSMAN

(57) ABSTRACT

Electrolytic gas generator and multi-functional current collector for use in same. In one embodiment, the current collector is constructed both to conduct current from an electrode to a conductive lead and to conduct gas generated at the electrode to external tubing. Accordingly, the current collector may be formed by bonding together a top metal plate and a bottom metal plate of similar profiles, each of which may be shaped to include a main portion and a lateral extension. The bottom metal plate may have central through hole in the main portion for receiving gas from the anode. The top metal plate may have a recess on its bottom surface. The recess may have a first end aligned with the through hole on the bottom metal plate and may have a second end at the end of the lateral extension. A lead and tubing may be attached to the lateral extension.

43 Claims, 25 Drawing Sheets

(51) Int. Cl.
*A61M 5/142* (2006.01)
*C25B 9/73* (2021.01)
*A61M 5/00* (2006.01)

(52) U.S. Cl.
CPC ............... *A61M 2005/006* (2013.01); *A61M 2005/14204* (2013.01); *A61M 2202/0208* (2013.01)

(56) References Cited

U.S. PATENT DOCUMENTS

| | | |
|---|---|---|
| 3,282,875 A | 11/1966 | Connolly et al. |
| 3,373,057 A | 3/1968 | Jost et al. |
| 3,453,086 A | 7/1969 | Harm |
| 3,783,868 A | 1/1974 | Bokros |
| 3,933,526 A | 1/1976 | Rackin |
| 4,057,479 A | 11/1977 | Campbell |
| 4,193,860 A | 3/1980 | Folser |
| 4,212,714 A | 7/1980 | Coker |
| 4,214,958 A | 7/1980 | Coker et al. |
| 4,233,146 A | 11/1980 | Rothmayer et al. |
| 4,341,604 A | 7/1982 | DeNora et al. |
| 4,343,690 A | 8/1982 | de Nora |
| 4,470,889 A | 9/1984 | Ezzell et al. |
| 4,478,695 A | 10/1984 | Ezzell et al. |
| 4,510,473 A | 4/1985 | Schweiger et al. |
| 4,520,254 A | 5/1985 | Steiger et al. |
| 4,539,539 A | 9/1985 | Schweiger et al. |
| 5,011,472 A | 4/1991 | Aebischer et al. |
| 5,026,615 A | 6/1991 | Tucholski |
| 5,338,662 A | 8/1994 | Sadri |
| 5,356,771 A | 10/1994 | O'Dell |
| 5,362,622 A | 11/1994 | O'Dell et al. |
| 5,385,821 A | 1/1995 | O'Dell et al. |
| 5,586,438 A | 12/1996 | Fahy |
| 5,788,682 A | 8/1998 | Maget |
| 5,951,538 A | 9/1999 | Joshi et al. |
| 5,965,433 A | 10/1999 | Gardetto et al. |
| 6,010,317 A | 1/2000 | Maget et al. |
| 6,060,640 A | 5/2000 | Pauley et al. |
| 6,171,368 B1 | 1/2001 | Maget et al. |
| D453,828 S | 2/2002 | Brassil et al. |
| 6,368,592 B1 | 4/2002 | Colton et al. |
| 6,475,716 B1 | 11/2002 | Seki |
| 6,492,103 B1 | 12/2002 | Taylor |
| 6,492,431 B1 | 12/2002 | Cisar et al. |
| 6,673,594 B1 | 1/2004 | Owen et al. |
| 6,677,150 B2 | 1/2004 | Alford et al. |
| 6,773,458 B1 | 8/2004 | Brauker et al. |
| 6,811,905 B1 | 11/2004 | Cropley et al. |
| 6,824,915 B1 | 11/2004 | Pedicini |
| 6,852,441 B2 | 2/2005 | Milgate, Jr. et al. |
| 6,977,140 B1 | 12/2005 | Owen et al. |
| 6,994,954 B2 | 2/2006 | Taylor |
| 7,176,015 B2 | 2/2007 | Alford et al. |
| 7,316,857 B1 | 1/2008 | Swanson |
| 7,572,622 B2 | 8/2009 | Hassanein et al. |
| 7,651,835 B2 | 1/2010 | Hassanein et al. |
| 7,892,222 B2 | 2/2011 | Vardi et al. |
| 7,947,094 B2 | 5/2011 | Fiebig |
| 7,947,405 B2 | 5/2011 | Mittelsteadt et al. |
| 8,012,500 B2 | 9/2011 | Rotem et al. |
| 8,043,271 B2 | 10/2011 | Stern et al. |
| 8,083,821 B2 | 12/2011 | Tempelman et al. |
| 8,100,672 B2 | 1/2012 | Walavalkar et al. |
| 8,349,151 B2 | 1/2013 | Schmitt et al. |
| 8,647,393 B2 | 2/2014 | Marshall et al. |
| 8,784,389 B2 | 7/2014 | Stern et al. |
| 8,900,763 B2 | 12/2014 | Lundblad et al. |
| 9,357,764 B2 | 6/2016 | Tempelman et al. |
| 9,433,557 B2 | 9/2016 | Green et al. |
| 9,595,727 B2 | 3/2017 | Mittelsteadt et al. |
| 10,231,817 B2 | 3/2019 | Tempelman et al. |
| 10,266,808 B2 | 4/2019 | Kelly et al. |
| 10,272,179 B2 | 4/2019 | Martinson et al. |
| 10,557,691 B2 | 2/2020 | Stone et al. |
| 2001/0013469 A1 | 8/2001 | Shiepe et al. |
| 2002/0033333 A1 | 3/2002 | Riecke |
| 2003/0008192 A1 | 1/2003 | Freund et al. |
| 2003/0087427 A1 | 5/2003 | Colton et al. |
| 2004/0058432 A1 | 3/2004 | Owen et al. |
| 2005/0074657 A1 | 4/2005 | Rusta-Sallehy et al. |
| 2005/0136092 A1 | 6/2005 | Rotem et al. |
| 2005/0221161 A1 | 10/2005 | Komada et al. |
| 2005/0221269 A1 | 10/2005 | Taylor et al. |
| 2006/0160204 A1 | 7/2006 | Hassanein et al. |
| 2006/0292544 A1 | 12/2006 | Hassanein et al. |
| 2008/0187901 A1 | 8/2008 | Doorschodt et al. |
| 2008/0226750 A1 | 9/2008 | Roth et al. |
| 2008/0248350 A1 | 10/2008 | Little et al. |
| 2009/0012502 A1 | 1/2009 | Rotem et al. |
| 2009/0042072 A1 | 2/2009 | Vu et al. |
| 2009/0112170 A1 | 4/2009 | Wells et al. |
| 2009/0197240 A1 | 8/2009 | Fishman et al. |
| 2010/0108534 A1 | 5/2010 | Carlstrom, Jr. et al. |
| 2010/0130916 A1 | 5/2010 | Stern et al. |
| 2010/0196439 A1 | 8/2010 | Beck et al. |
| 2010/0204683 A1 | 8/2010 | Bodor et al. |
| 2010/0243434 A1 | 9/2010 | Maget |
| 2010/0330547 A1 | 12/2010 | Tempelman et al. |
| 2011/0008886 A1 | 1/2011 | Hering et al. |
| 2011/0054387 A1 | 3/2011 | Stern et al. |
| 2011/0212431 A1 | 9/2011 | Bunegin et al. |
| 2011/0295241 A1 | 12/2011 | Ziaie et al. |
| 2012/0209434 A1 | 8/2012 | Kurashina et al. |
| 2013/0040223 A1 | 2/2013 | Tsukamoto et al. |
| 2013/0264218 A1 | 10/2013 | Vinton et al. |
| 2014/0257515 A1 | 9/2014 | So et al. |
| 2015/0112247 A1 | 4/2015 | Tempelman et al. |
| 2018/0133383 A1 | 5/2018 | Ferrante et al. |
| 2018/0135948 A1 | 5/2018 | Stone et al. |
| 2018/0318566 A1 | 11/2018 | Ferrante et al. |
| 2019/0119462 A1 | 4/2019 | Desai et al. |
| 2019/0125668 A1 | 5/2019 | Fox et al. |
| 2019/0125937 A1 | 5/2019 | Rotem |

FOREIGN PATENT DOCUMENTS

| | | |
|---|---|---|
| CN | 101053104 A | 10/2007 |
| CN | 101569559 A | 11/2009 |
| CN | 104185918 A | 12/2014 |
| EP | 0470726 A1 | 2/1992 |
| EP | 3541450 B1 | 12/2021 |
| JP | H07196401 A | 8/1995 |
| JP | 2001011680 A | 1/2001 |
| JP | 2001176519 A | 6/2001 |
| JP | 2008519830 A | 6/2008 |
| WO | 0121234 A1 | 3/2001 |
| WO | 0150983 A1 | 7/2001 |
| WO | 2006112720 A2 | 10/2006 |
| WO | 2006122169 A2 | 11/2006 |
| WO | 2008079997 A2 | 7/2008 |
| WO | 2009031154 A2 | 3/2009 |
| WO | 2009094236 A2 | 7/2009 |
| WO | 2010049996 A1 | 5/2010 |
| WO | 2011159246 A1 | 12/2011 |
| WO | 2015048184 A1 | 4/2015 |
| WO | 2018085714 A1 | 5/2018 |
| WO | 2018102077 A2 | 6/2018 |
| WO | 2018144098 A1 | 8/2018 |
| WO | 2018144099 A1 | 8/2018 |
| WO | 2019067766 A1 | 4/2019 |
| WO | 2019089943 A1 | 5/2019 |

OTHER PUBLICATIONS

Written Opinion dated Aug. 6, 2019, from PCT Application No. PCT/US2019/032990, the corresponding PCT application to the present application.

"Gore Technologies" (Gore) Nov. 12, 2016 (Nov. 12, 2016) [online] retrieved from <URL:https://web.archive.org/web/20161112003850/https://www.gore.com/about/technologies>.

(56) References Cited

OTHER PUBLICATIONS

Abstract of Kanehashi et al., "Gas and Vapor Transport in Membranes," Membrane Characterization, 309-336 (2017).
Zeman et al., "Evaluation of Oxygen Permeability of Polyethylene Films," Technical Sciences, 15(2): 331-345 (2012).
Tibell et al., "Survival of Macroencapsulated Allogenic Parathyroid Tissue One Year After Transplantation in Nonimmunosuppressed Humans," Cell Transplantation, 10:591-9 (2001).
Pedraza et al., "Preventing hypoxia-induced cell death in beta cells and islets via hydrolytically activated, oxygen-generating biomaterials," PNAS, 109(11):4245-4250 (2012).
Ludwig et al., "Improvement of islet function in a bioartificial pancreas by enhanced oxygen supply and growth hormone releasing hormone agonist," PNAS, 109(13):5022-5027 (2012).
Tarantal et al., "Real-time Bioluminescence Imaging of Macroencapsulated Fibroblasts Reveals Allograft Protection in Rhesus Monkeys (Macaca mulatta)," Transplantation, 88(1):38-41 (2009).
Colton, "Oxygen supply to encapsulated therapeutic cells," Advanced Drug Delivery Reviews, 67-68:93-110 (Feb. 27, 2014).
Weir, "Islet encapsulation: advances and obstacles," Diabetologia, 56:1458-1461 (Apr. 30, 2013).
Ludwig et al., "Transplantation of human islets without immunosuppression," PNAS, 110(47):19054-19058 (Nov. 19, 2013).
Ohsawa et al., "Hydrogen acts as a therapeutic antioxidant by selectively reducing cytotoxic oxygen radicals," Nature Medicine, 13(6):688-694 (2007).
Burns et al., "The Survival of Mammalian Tissues Perfused with Intravascular Gas Mixtures of Oxygen and Carbon Dioxide," Can. J. Biochem. Physiol., 36:499-504 (1958).
Neufeld et al., "The Efficacy of an Immunoisolating Membrane System for Islet Xenotransplantation in Minipigs," PLoS ONE, 8(8):e70150 (pp. 1-13) (Aug. 1, 2013).
Wood et al., "The hydrogen highway to reperfusion therapy," Nature Medicine, 13(6):673-674 (2007).
Saad et al., "Extension of Ischemic Tolerance of Porcine Livers by Cold Preservation Including Postconditioning with Gaseous Oxygen," Transplantation, 71:498-502 (2001).
Kin et al., "Islet Isolation and Transplantation Outcomes of Pancreas Preserved with University of Wisconsin Solution Versus Two-Layer Method Using Preoxygenated Perfluorocarbon," Transplantation, 82(10):1286-1290 (2006).
Sudan et al., "A New Technique for Combined Liver/Small Intestinal Transplantation," Transplantation, 72(11):1846-1848 (2001).
Kuhn-Regnier et al., "Coronary oxygen persufflation combined with HTK cardioplegia prolongs the preservation time in heart transplantation," European Journal of Cardio-thoracic Surgery, 17:71-76 (2000).
Hunt et al., "Cannulation of the portal vein for cytotoxic liver perfusion in colorectal carcinomas: an alternative approach," Annals of the Royal College of Surgeons of England, 68:36-38 (1986).
Wu et al., "In Situ Electrochemical Oxygen Generation with an Immunoisolation Device," Ann. N.Y. Acad. Sci., pp. 105-125 (1999).
Moers et al., "Machine Perfusion or Cold Storage in Deceased-Donor Kidney Transplantation," N. Eng. J. Med., 360:7-19 (2009).
Emamaullee et al., "Caspase Inhibitor Therapy Synergizes With Costimulation Blockade to Promote Indefinite Islet Allograft Survival," Diabetes, 59:1469-77 (2010).
Emamaullee et al., "The Caspase Selective Inhibitor EP1013 Augments Human Islet Graft Function and Longevity in Marginal Mass Islet Transplantation in Mice," Diabetes, 57:1556-66 (2008).
Expanding Transplantation Possibilities, Lifeline Scientific Annual Report 2010, Lifeline Scientific, Inc., Itasca, Illinois.
Calhoon et al., "Twelve-Hour Canine Heart Preservation With a Simple, Portable Hypothermic Organ Perfusion Device," Ann. Thorac. Surg., 62:91-3 (1996).
Hassanein et al., "Continuous Perfusion of Donor Hearts in the Beating State Extends Preservation Time and Improves Recovery of Function," J. Thorac. Cardiovasc. Surg., 116:821-30 (1998).

Weegman et al., "Continuous Real-Time Viability Assessment of Kidneys Based on Oxygen Consumption," Transplant Proc., 42(6):2020-2023 (2010).doi:10.1016/j.transproceed.2010.05.082.
Suszynski et al., "Persufflation (or gaseous oxygen perfusion) as a method of organ preservation," Cryobiology, 64(3):125-143 (2012).
Scott et al., "Pancreas Oxygen Persufflation Increases ATP Levels as Shown by Nuclear Magnetic Resonance," Transplantation Proceedings, 42(6): 2011-2015 (Jul.-Aug. 2010).
Fischer, "Methods of Cardiac Oxygen Persufflation," Methods in Bioengineering: Organ Preservation and Reengineering, editors Korkut Uygun and Charles Y. Lee, published by Artech House, Norwood, MA (2011).
Treckmann et al., "Retrograde Oxygen Persufflation Preservation of Human Livers: A Pilot Study," Liver Transplantation, 14:358-64 (2008).
Koetting et al., "Optimal Time for Hypothermic Reconditioning of Liver Grafts by Venous Systemic Oxygen Persufflation in a Large Animal Model," Transplantation, 91(1):42-7 (2011).
Guibert et al., "Organ Preservation: Current Concepts and New Strategies for the Next Decade," Transfusion Medicine and Hemotherapy, 38:125-142 (2011).
Caballero-Corbalan et al., "No Beneficial Effect of Two-Layer Storage Compared with UW-Storage on Human Islet Isolation and Transplantation," 84(7):864-9 (2007).
Minor et al., "Energetic recovery in porcine grafts by minimally invasive liver oxygenation," Journal of Surgical Research, published online Mar. 14, 2012.
Taylor et al., "Current state of hypothermic machine perfusion preservation of organs: The clinical perspective," Cryobiology (2009), doi:10.1016/j.cryobiol.2009.10.006.
Scott et al., "Persufflation Improves Pancreas Preservation When Compared With the Two-Layer Method," Transplantation Proceedings, 42(6): 2016-2019 (Jul.-Aug. 2010).
J.H. Fischer: Methods of Cardiac Oxygen Persufflation. Author manuscript available at ResearchGate.net Mar. 15, 2018. Published in final edited form as: Methods of Bioengineering: Organ preservation and reengineering. Eds. Korkut Uygun and Charles Y. Lee. Artech House Boston, London 2011, p. 105-126. ISBN: 13: 978-1-60807-013-8.
Avgoustiniatos et al., "Effect of External Oxygen Mass Transfer Resistances on Viability of Immunoisolated Tissue," Ann NY Acad Sci, 831:145-167 (1997).
Barkai et al., "Enhanced Oxygen Supply Improves Islet Viability in a New Bioartificial Pancreas," Cell Transplantation, 22:1463-1476 (2013).
Bellin et al., "Potent induction immunotherapy promotes long-term insulin independence after islet transplantation in type 1 diabetes," Am J Transplant., 12(6):1576-1583 (2012).
Bergenstal et al., "Effectiveness of Sensor-Augmented Insulin-Pump Therapy in Type 1 Diabetes," N Eng J Med, 363(4):311-320 (2010).
Goh et al., "Dual Perfluorocarbon Method to Noninvasively Monitor Dissolved Oxygen Concentration in Tissue Engineered Constructs in vitro and in vivo," Biotechnol. Prog., 27:1115-1125 (2011).
Goh et al., "In Vivo Noninvasive Monitoring of Dissolved Oxygen Concentration Within an Implanted Tissue-Engineered Pancreatic Construct," Tissue Engineering: Part C, 17(9):887-894 (2011).
Klonoff et al., "Innovations in Technology for the Treatment of Diabetes: Clinical Development of the Artificial Pancreas (an Autonomous System)," Journal of Diabetes Science and Technology, 5(3):804-826 (2011).
Ludwig et al., "A Novel Device for Islet Transplantation Providing Immune Protection and Oxygen Supply," Horm Metab Res, 42:918-922 (2010).
Luo et al., Recovery of Neurological Functions in Non-Human Primate Model of Parkinson's Disease by Transplantation of Encapsulated Neonatal Porcine Choroid Plexus Cells, Journal of Parkinson's Disease, 3: 275-291 (2013).
O'Sullivan et al., "Islets Transplanted in Immunoisolation Devices: A Review of the Progress and the Challenges that Remain," Endocrine Reviews, 32(6):827-844 (2011).

(56) References Cited

OTHER PUBLICATIONS

Ritz-Laser et al., "Molecular Detection of Circulating Beta-Cells After Islet Transplantation," Diabetes, 51:557-561 (2002).
Storrs et al., "Preclinical Development of the Islet Sheet," Ann NY Acad Sci, 944:252-266 (2001).
Wang et al., "Donor Treatment With Carbon Monoxide Can Yield Islet Allograft Survival and Tolerance," Diabetes, 54:1400-1406 (2005).

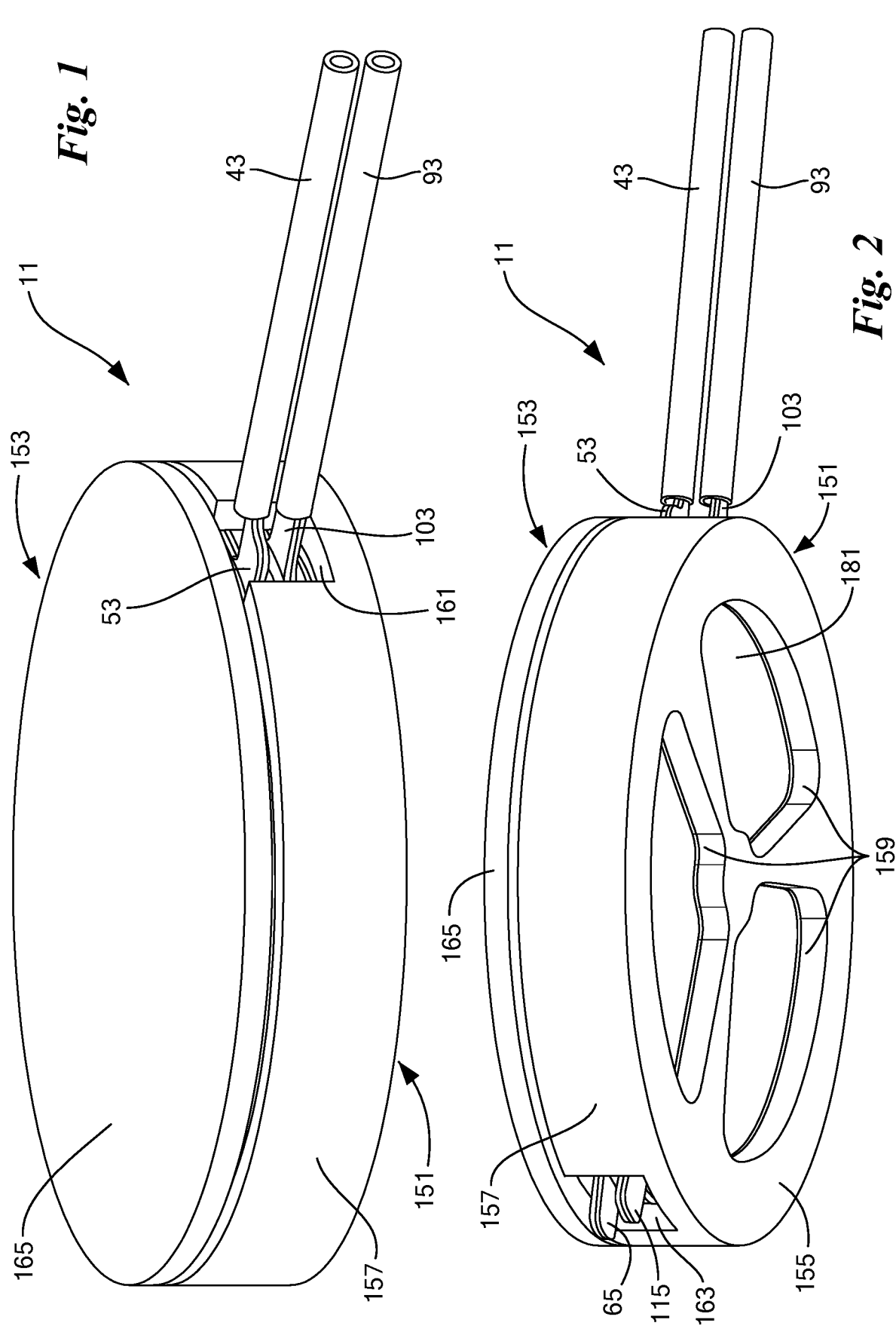

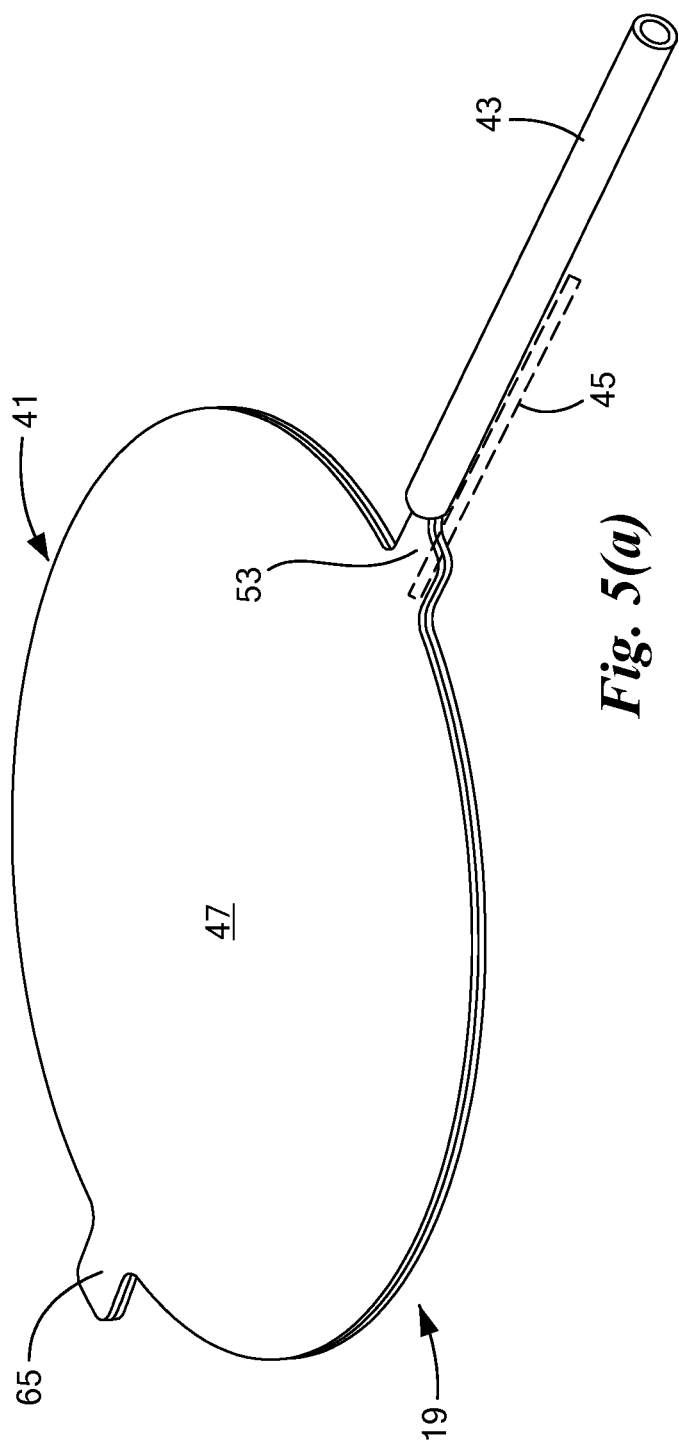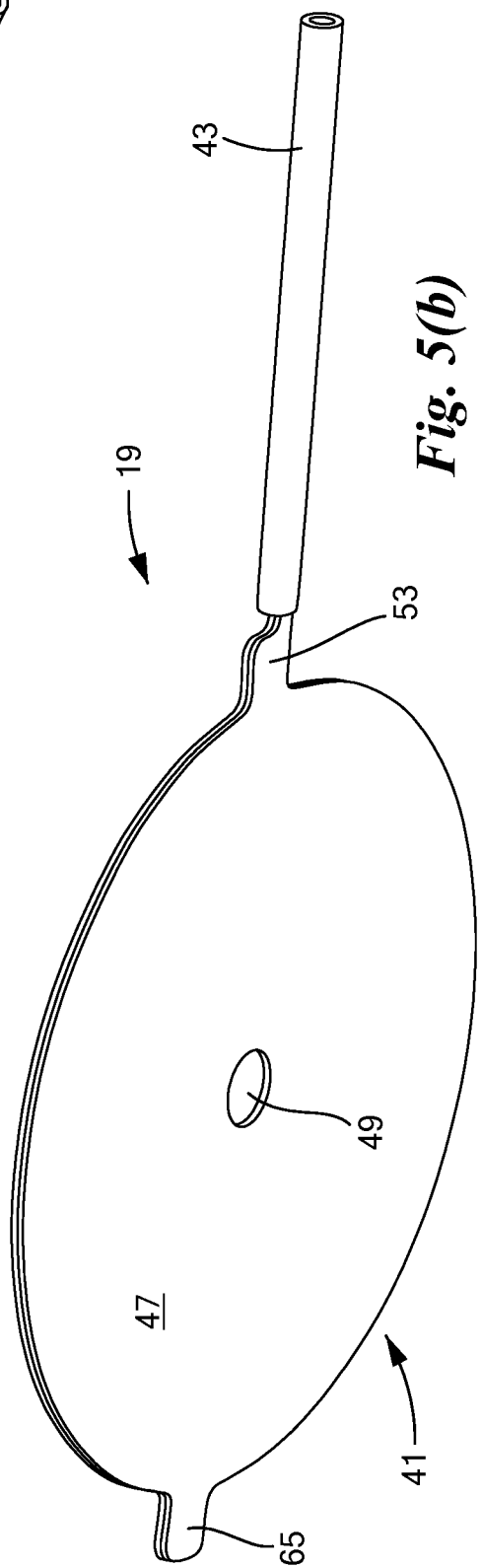

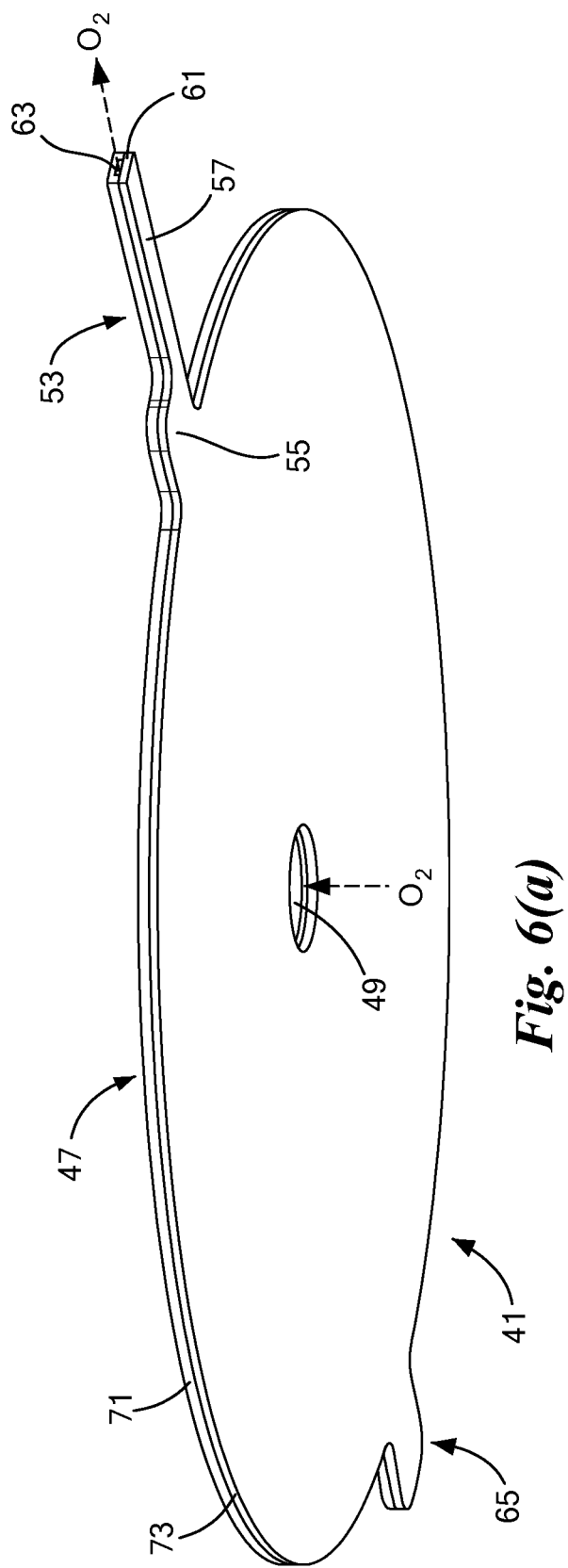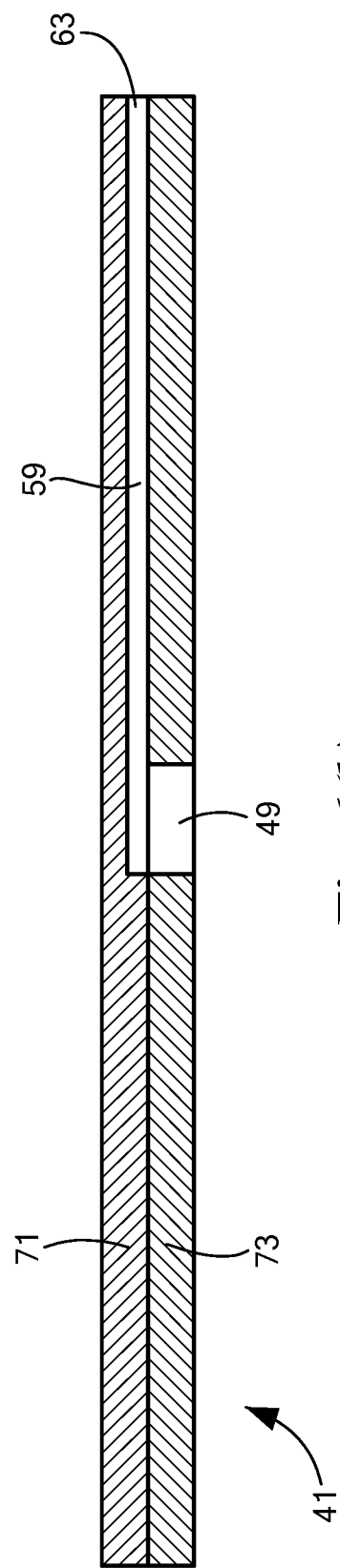

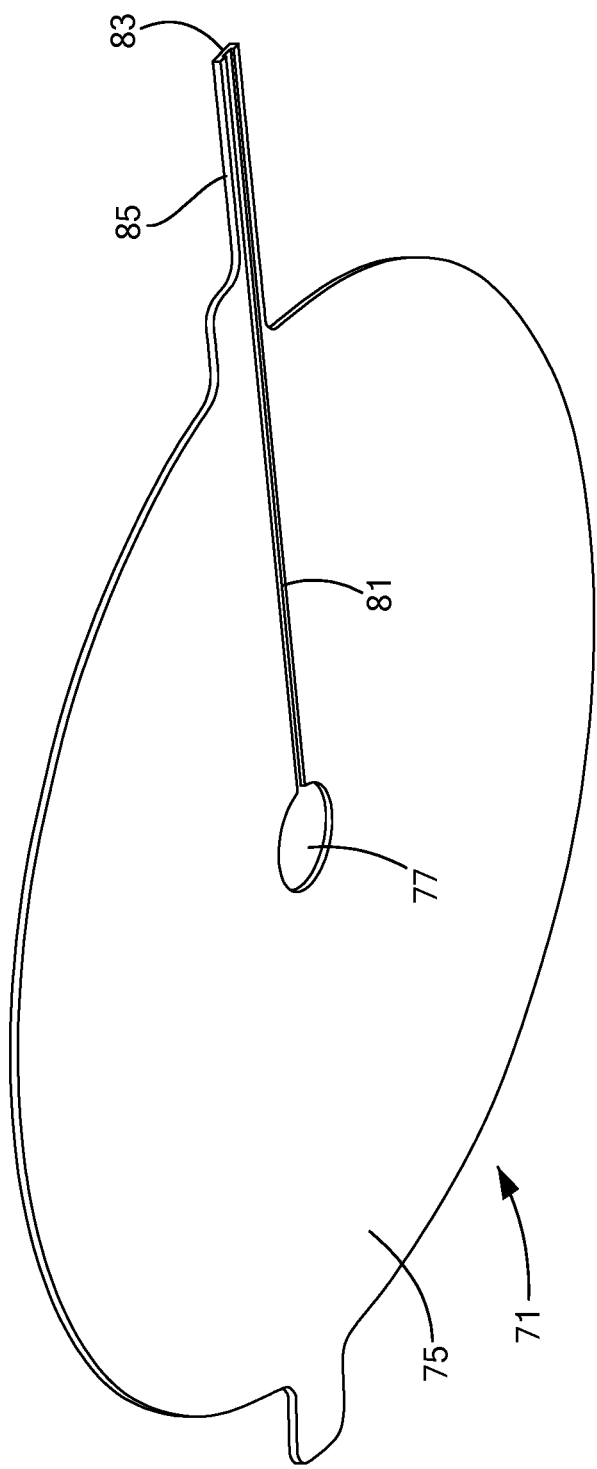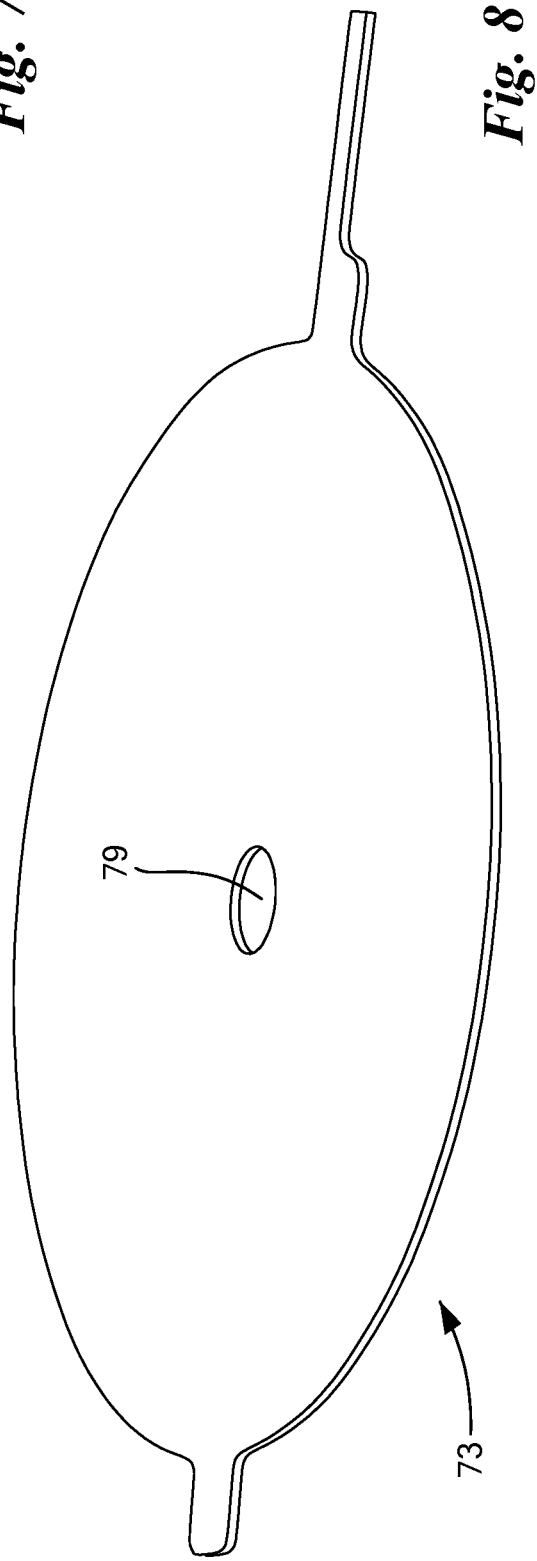

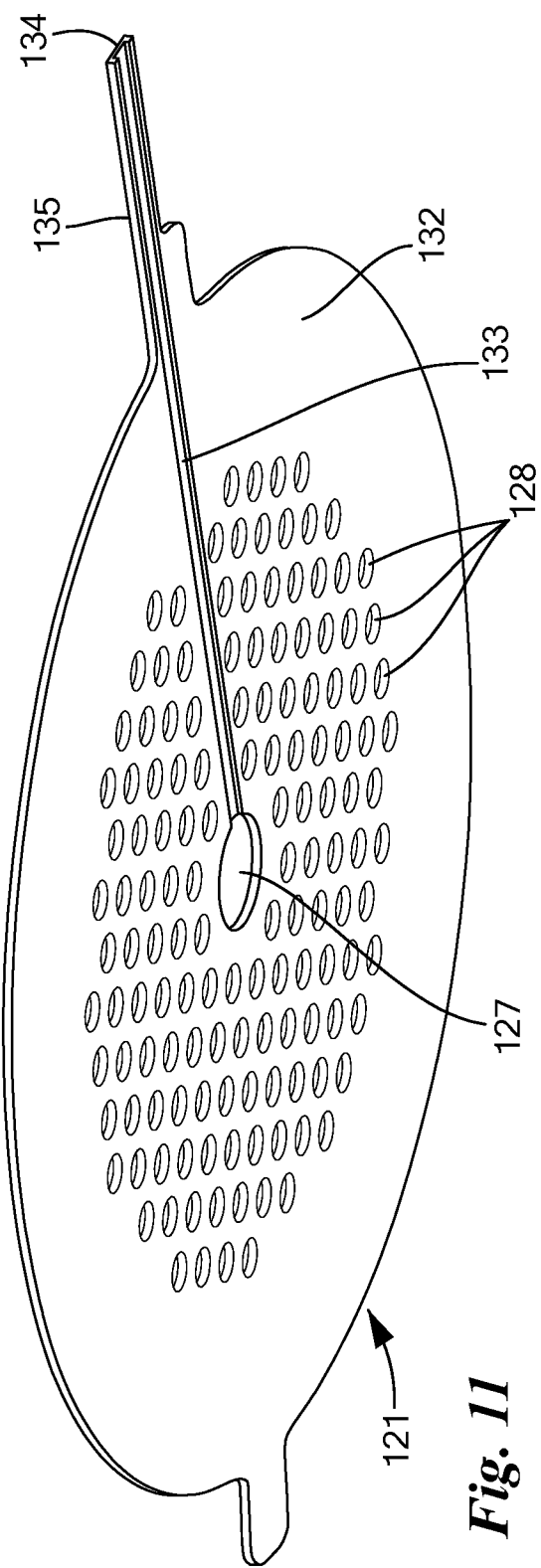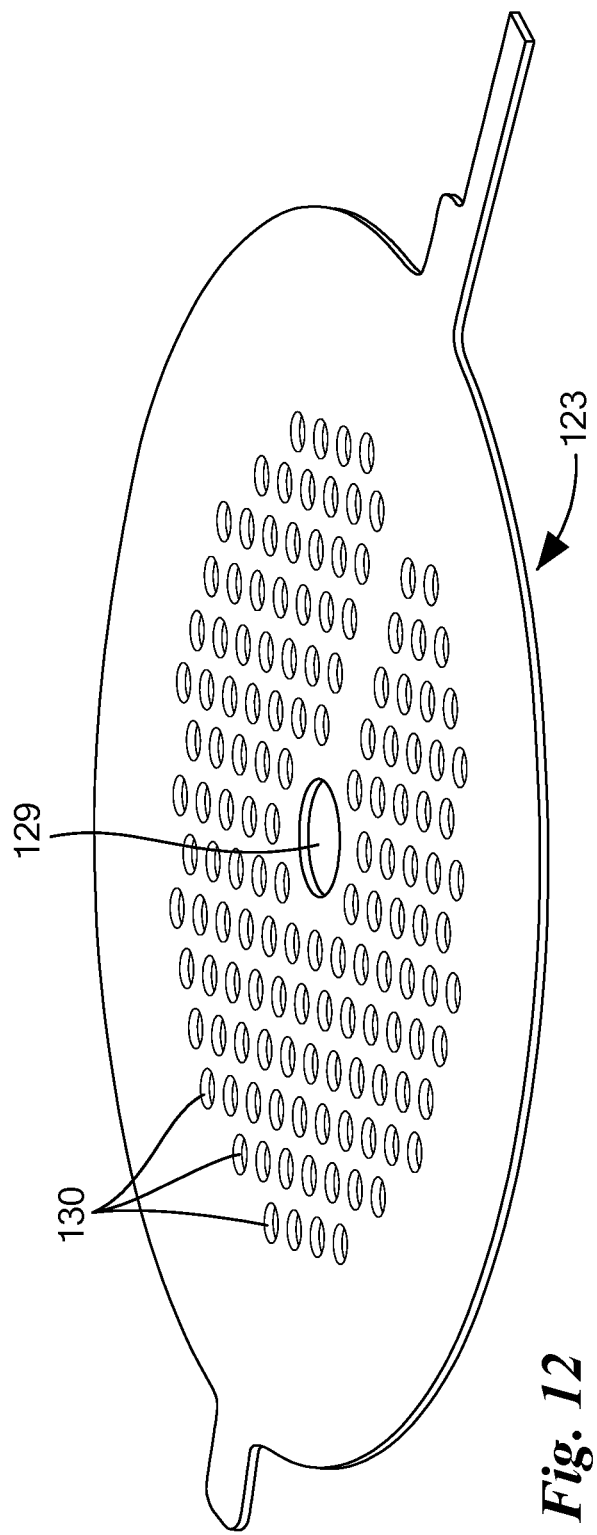

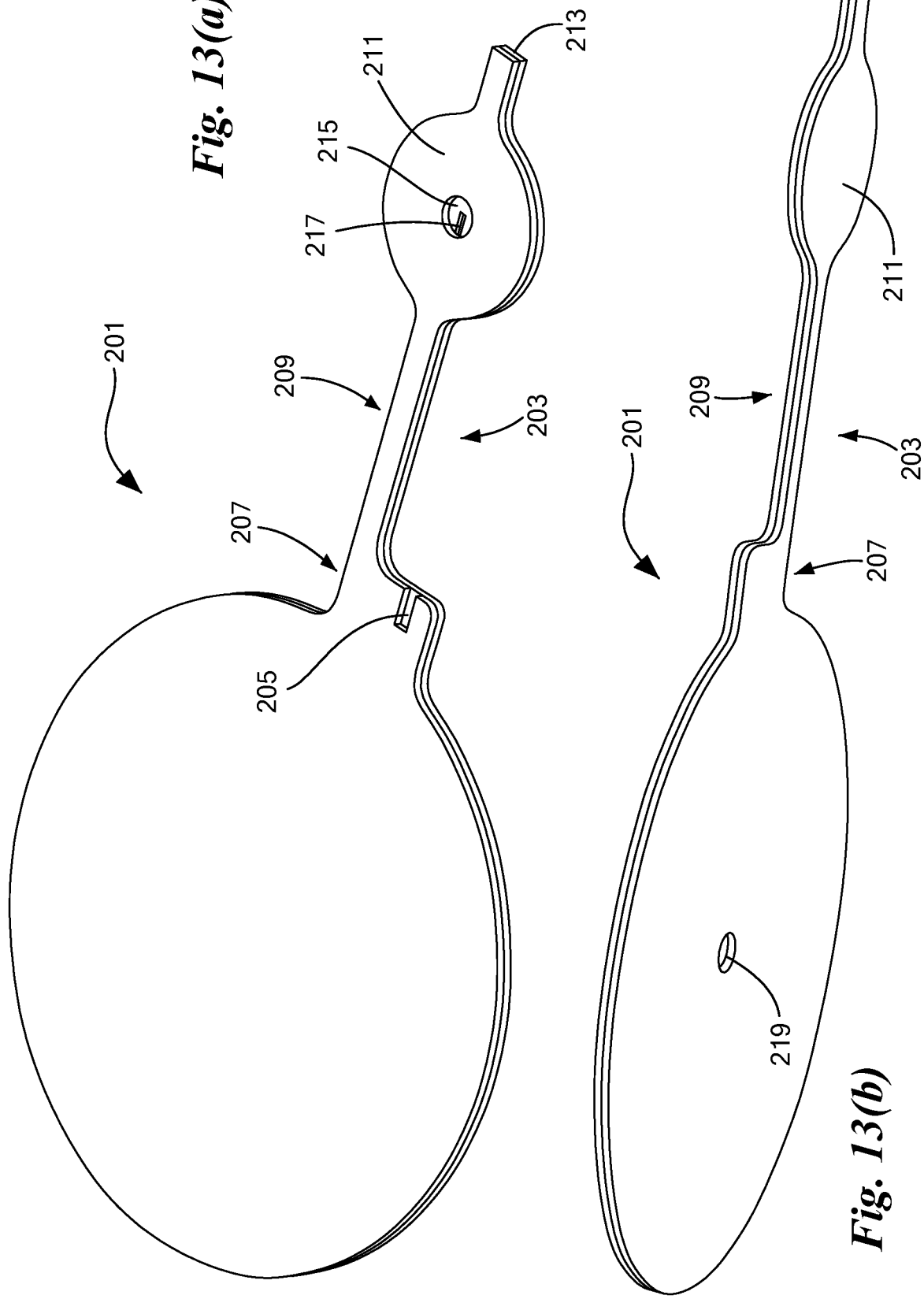

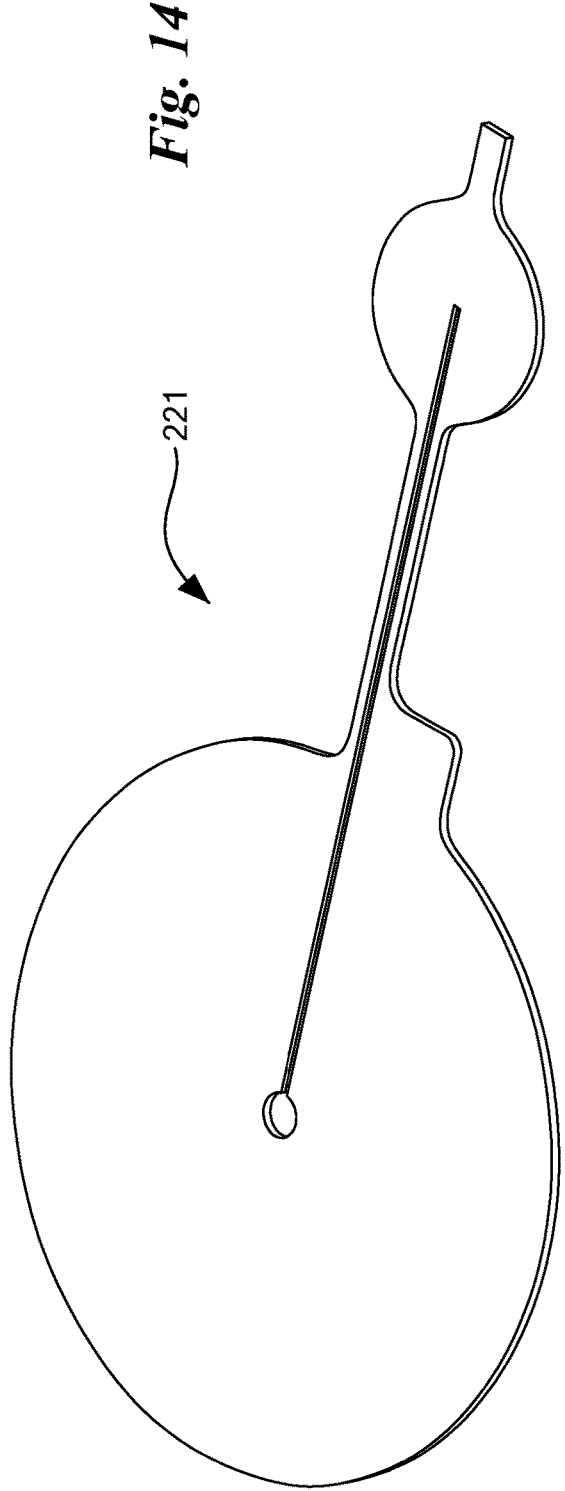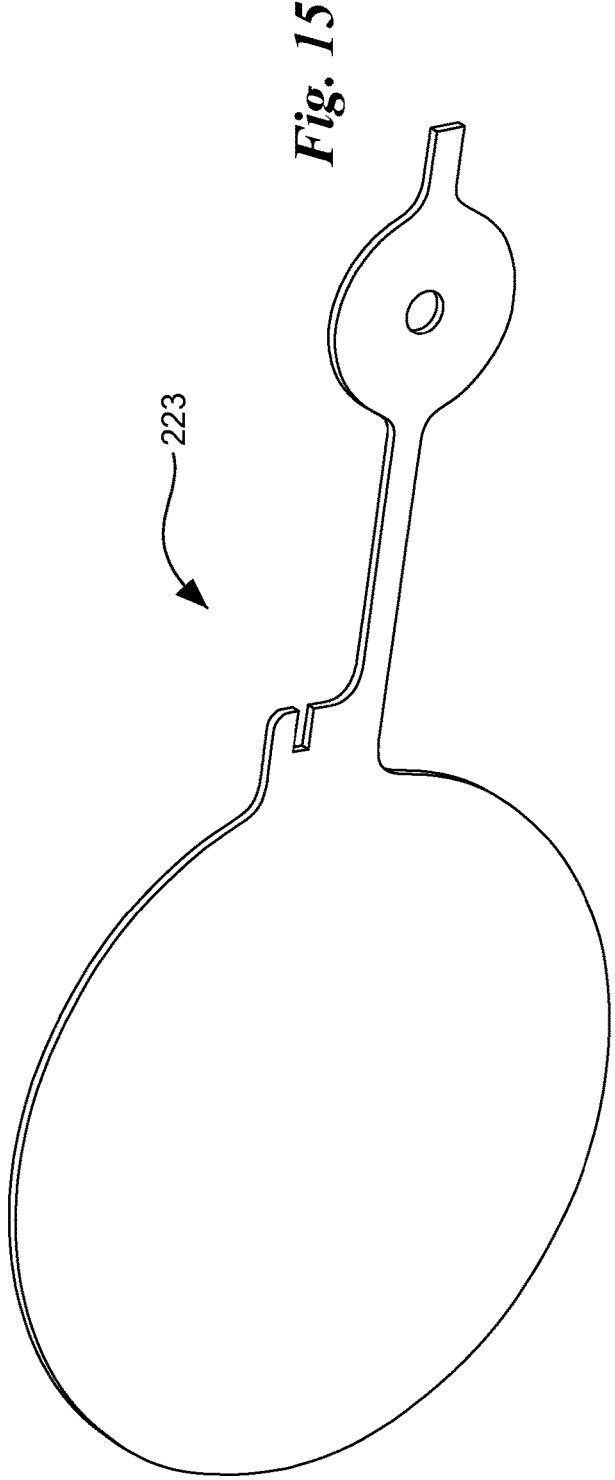

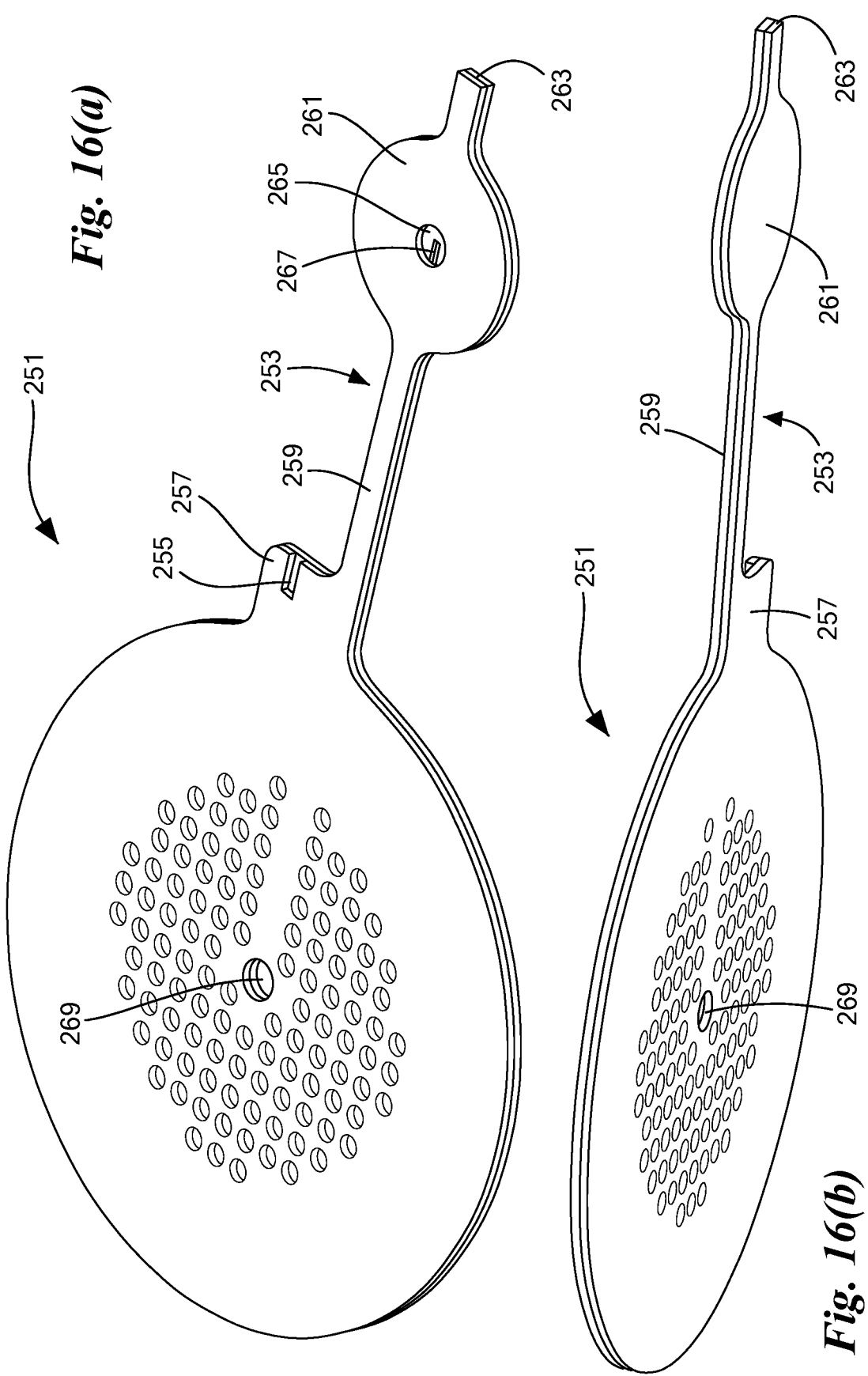

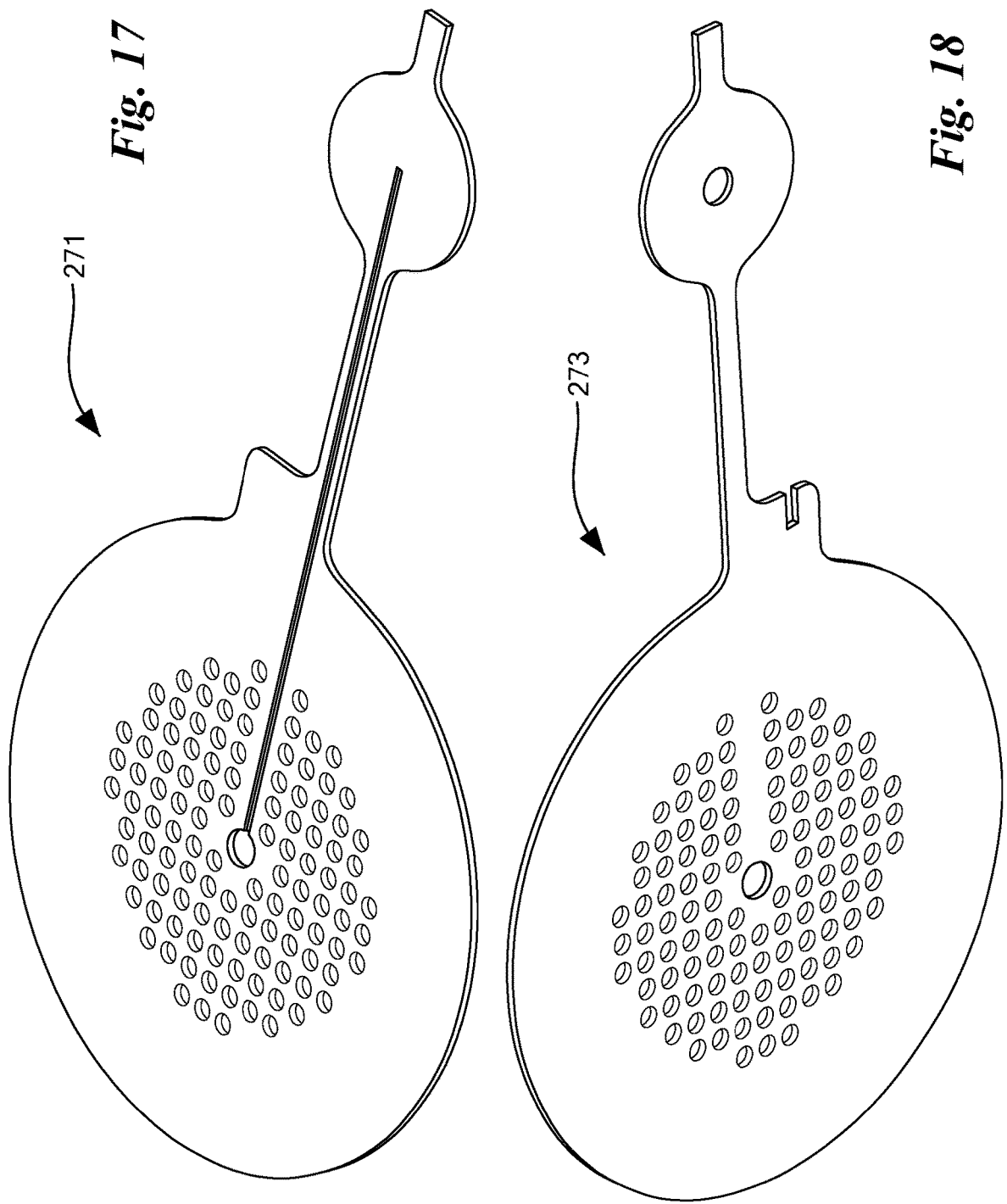

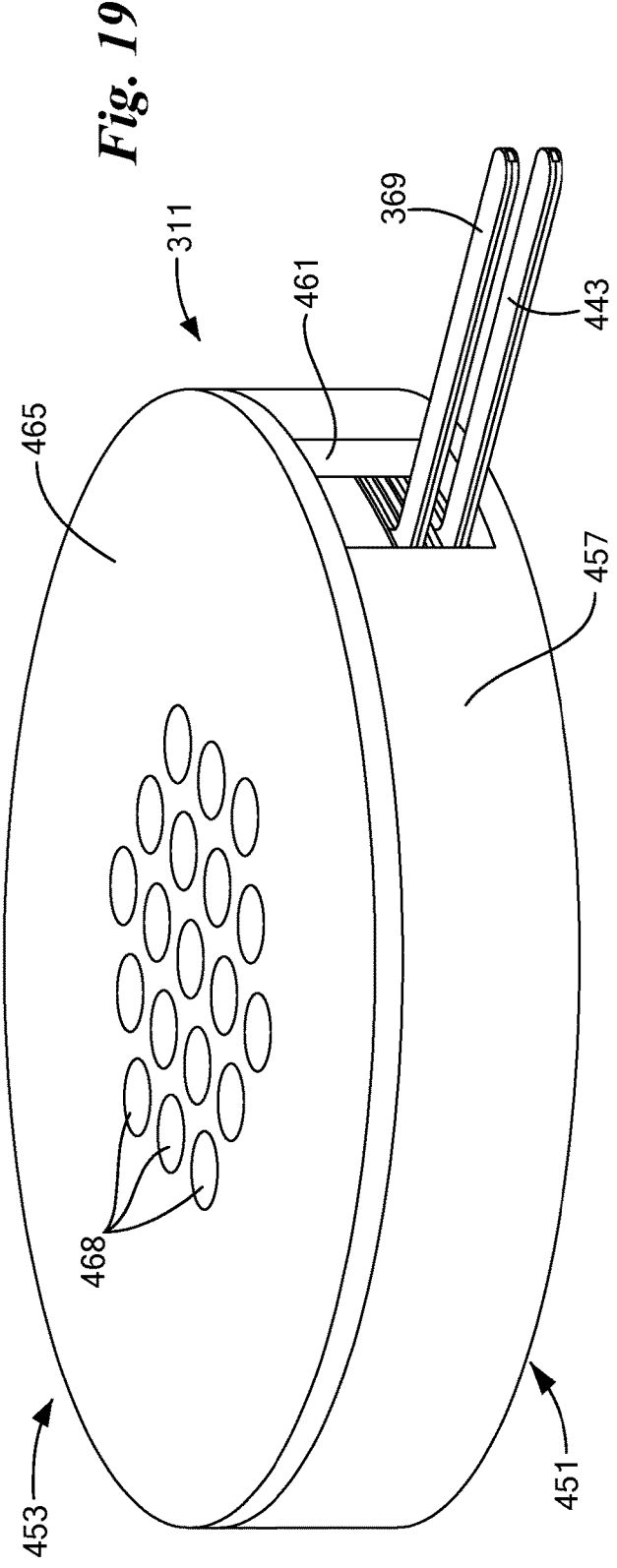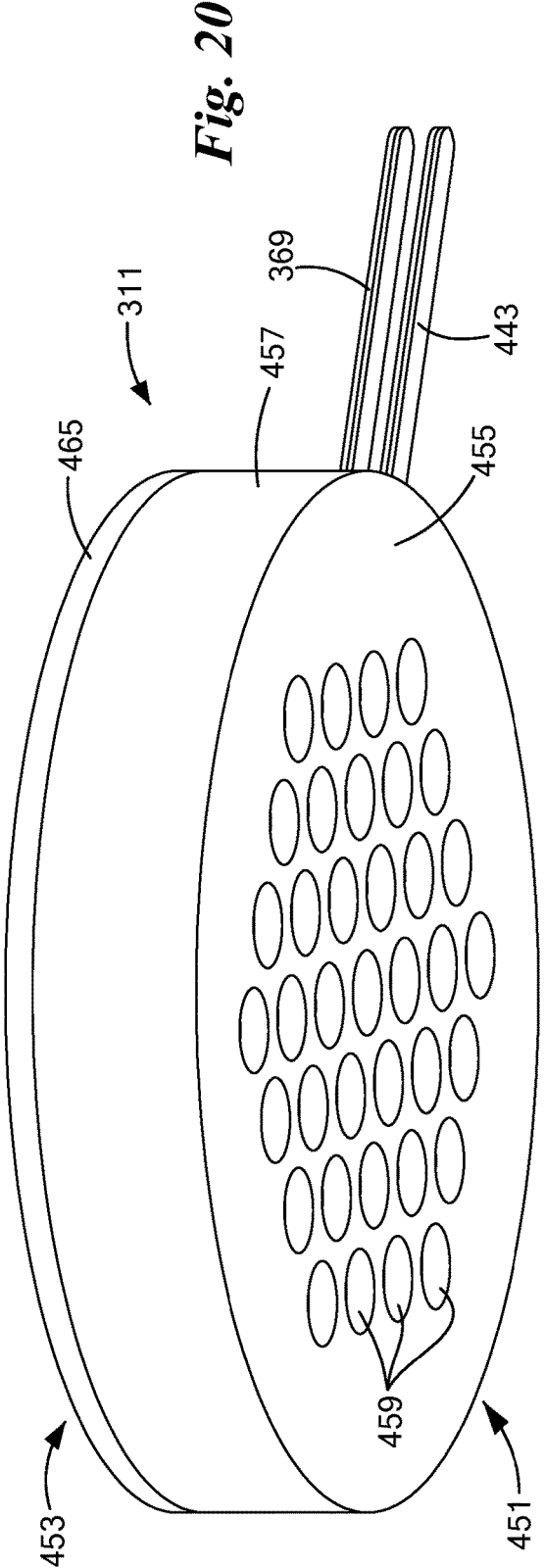

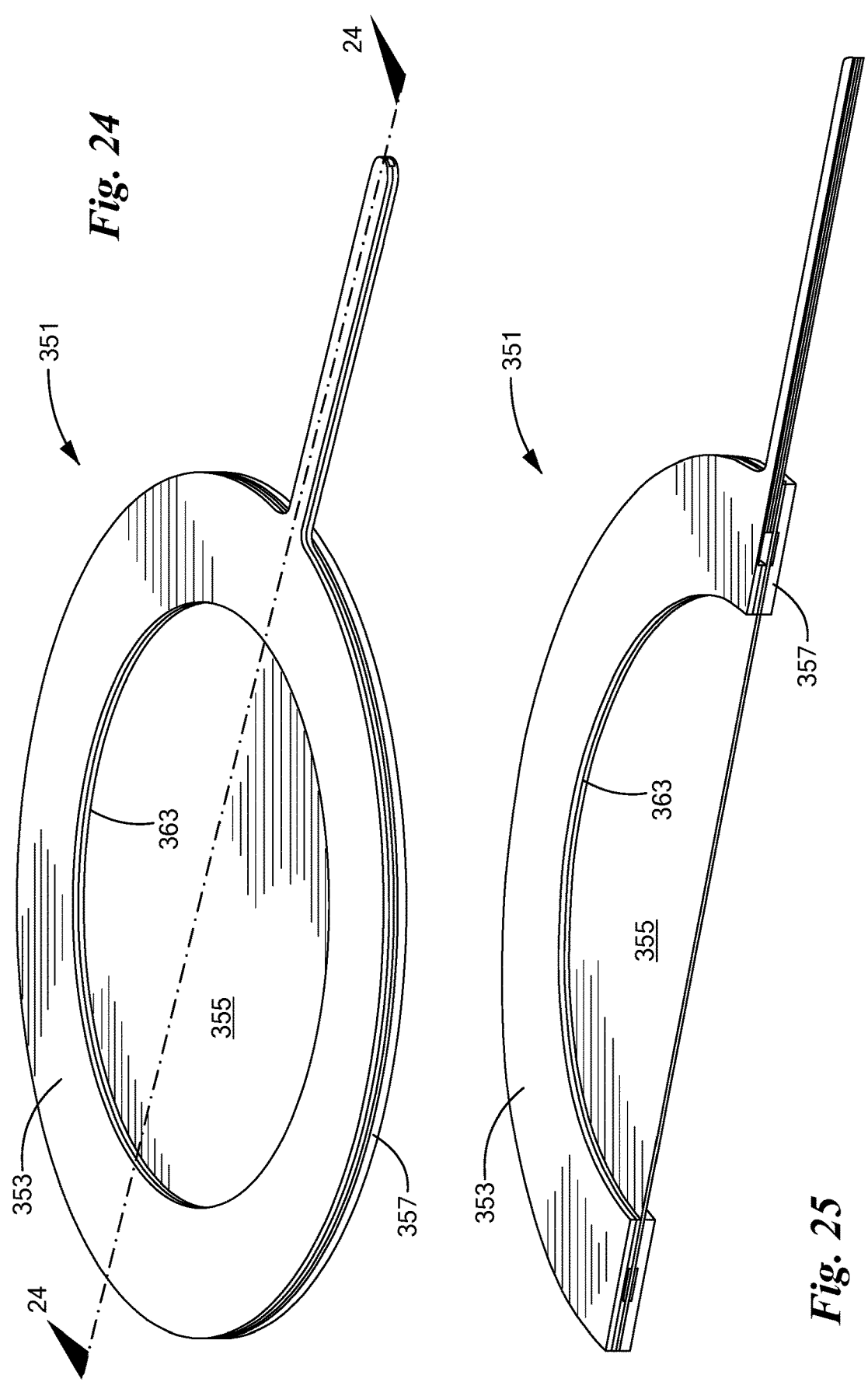

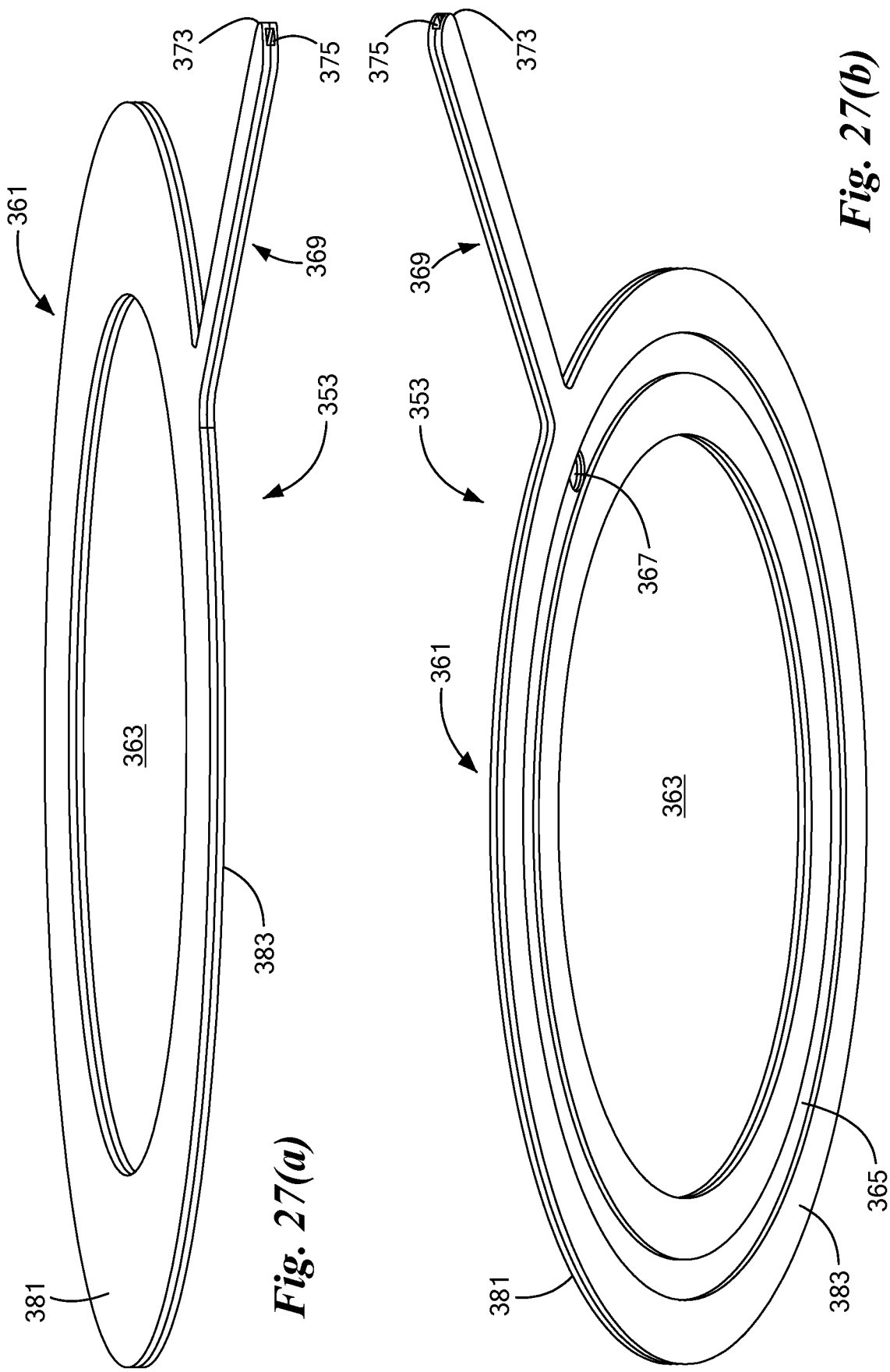

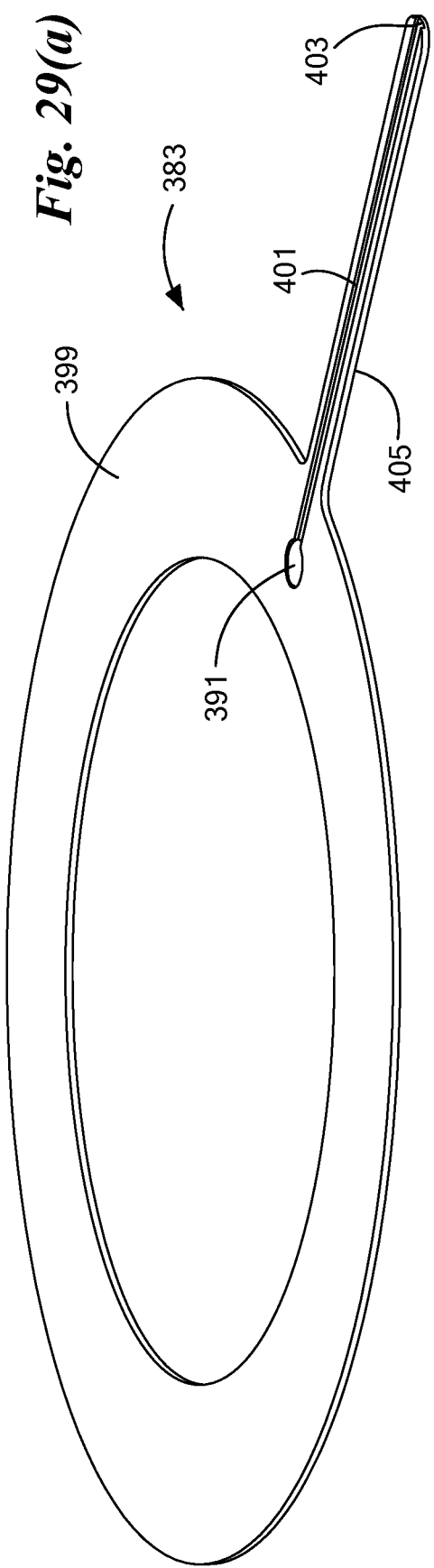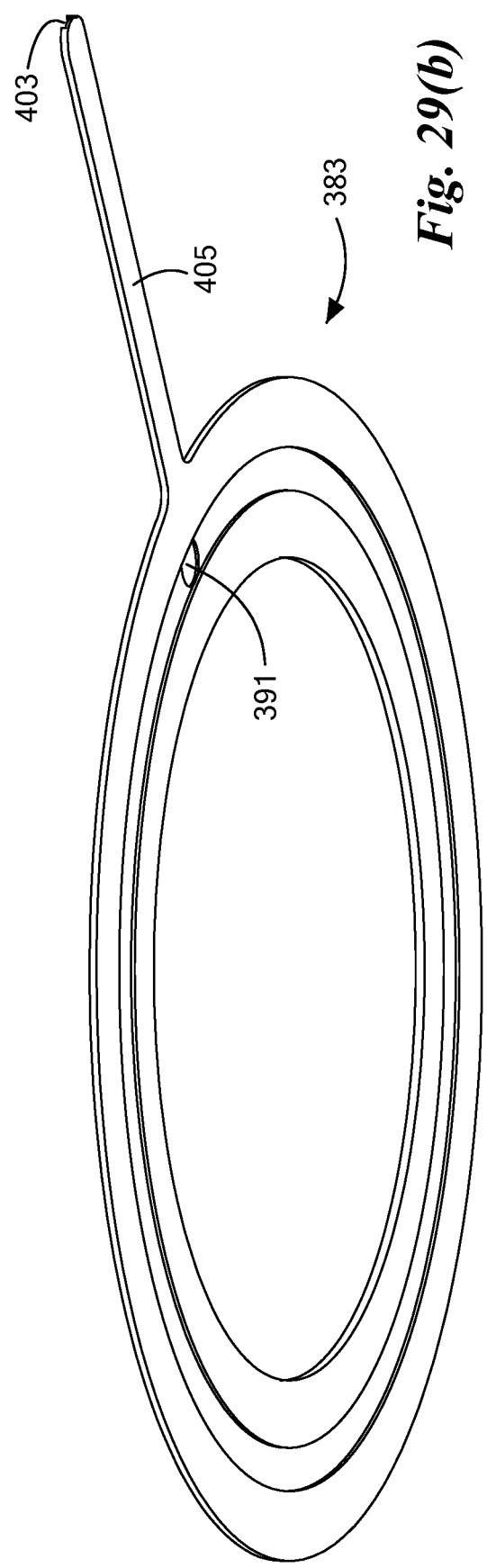

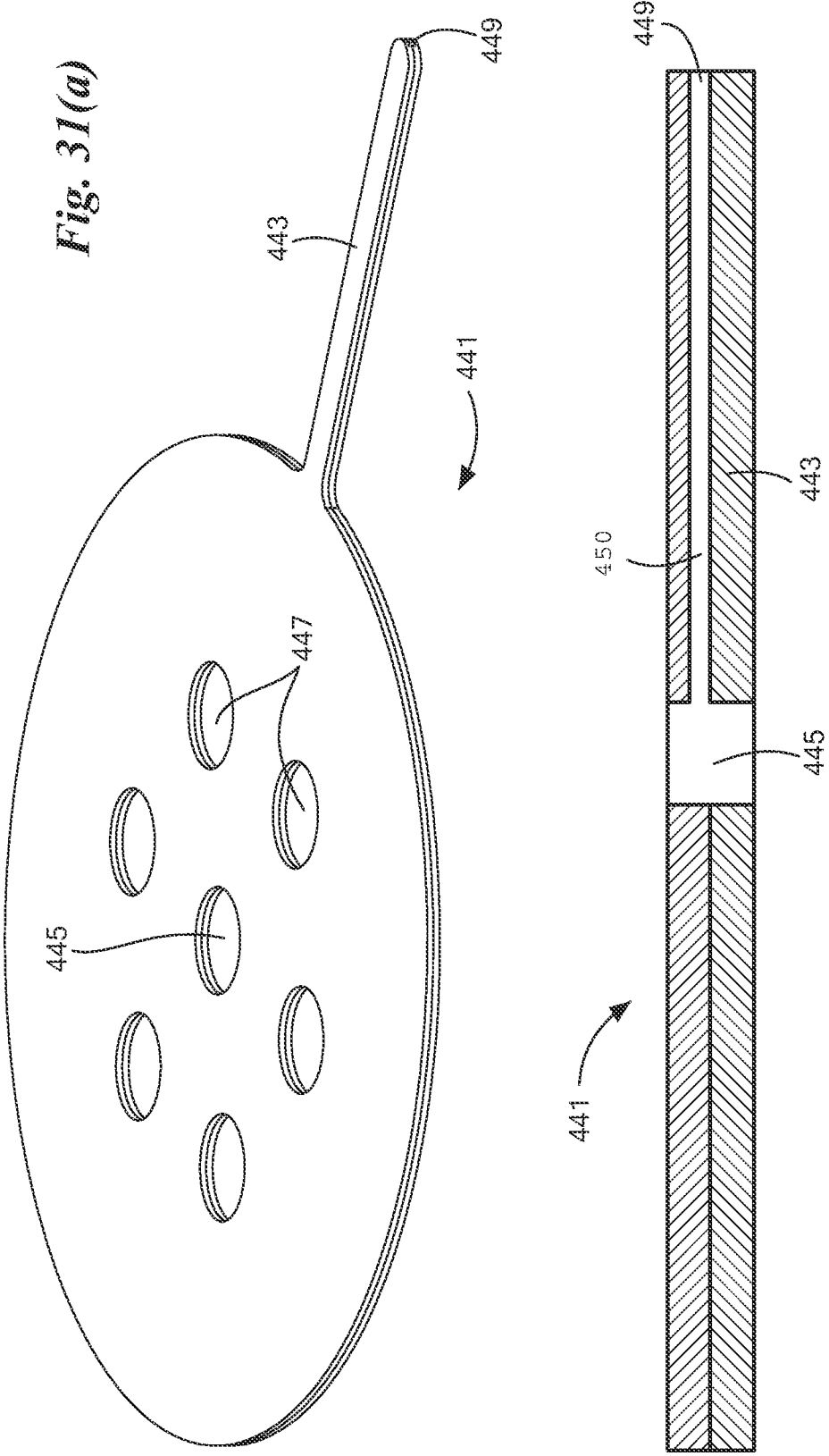

COMBINED ELECTRICAL LEAD AND GAS PORT TERMINALS AND ELECTROLYTIC GAS GENERATOR COMPRISING SAME

CROSS-REFERENCE TO RELATED APPLICATIONS

The present application claims the benefit under 35 U.S.C. 119(e) of U.S. Provisional Patent Application No. 62/672,784, inventors Melissa N. Schwenk et al., filed May 17, 2018, the disclosure of which is incorporated herein by reference in its entirety.

FEDERALLY SPONSORED RESEARCH OR DEVELOPMENT

This invention was made with government support under R44 DK100999 and R43 DK113536 awarded by National Institutes of Health. The government has certain rights in the invention.

BACKGROUND OF THE INVENTION

The present invention relates generally to electrolytic gas generators and relates more particularly to a novel electrolytic gas generator and to combination electrical lead and gas port terminals for use therein.

The controlled generation of one or more types of gases at point-of-use is of significance to a multitude of industrial and medical applications. Electrolysis is a common technique for generating such gases and typically involves converting a feedstock (which is often a low cost, stable reactant) to a useful commodity (which is often a high cost or unstable product) using an electrical current. Electrolysis is favored as a production technique due to its high process efficiency, its product selectivity, and its inherent ability to control production rate by controlling the applied current. Devices designed to generate one or more gases using electrolysis are sometimes referred to as electrolytic gas generators. Electrolytic gas generators for hydrogen production, for instance, are used frequently in analytical laboratories to supply high purity hydrogen, on-demand, for use as carrier and detector gases in gas chromatographs. Electrolytic gas generators for oxygen production, for example, have been used to generate oxygen in situ at skin wounds to improve the healing process for severe burns and diabetic ulcers. Such electrolytic gas generators typically require several basic system components to govern performance and safety, and these basic system components generally include current control (e.g., a DC power supply for maintaining generation rate and voltage efficiency), downstream pressure and gas purity monitoring (e.g., for process and environmental safety), and fluid management (e.g., water reactant feed pump and gas-liquid separation units). However, as can be appreciated, such components can increase the size, cost, and complexity of the overall system and can make the overall system more difficult to maintain. Also, although hydrogen and oxygen are two of the more common gases produced by electrolytic gas generators, electrolytic gas generators can be used to produce other gases, such as, but not limited to, carbon dioxide, chlorine, ozone, hydrogen peroxide, chlorine dioxide, nitric oxide, sulfur dioxide, hydrogen sulfide, carbon monoxide, ammonia, hydrogen chloride, hydrogen bromide, and hydrogen cyanide.

An emerging medical application for in situ gas generation is in the provision of gaseous oxygen to cells and/or tissues that are located under the skin or that are included as part of a subdermal implant device. Subdermal implant devices are useful implements for the in situ generation and dissemination of therapeutics to a patient in need thereof for the treatment of various diseases, disorders, and/or conditions. Typically, such implant devices comprise cells and/or tissues that are encapsulated within a suitable implantable container. The implantable container is typically designed to allow the cells and/or tissues to produce the desired therapeutic and for the dissemination of the produced therapeutic to the patient while, at the same time, limiting an immunological response. As can be appreciated, the delivery of essential gases (e.g., oxygen) and nutrients to implant devices is important for the viability and function of the cells and/or tissues contained therein.

In U.S. Pat. No. 6,368,592 B1, inventors Colton et al., which issued Apr. 9, 2002, and which is incorporated herein by reference in its entirety, there is disclosed a method of delivering oxygen to cells by electrolyzing water. According to the aforementioned patent (hereinafter "the '592 patent"), oxygen is supplied to cells in vitro or in vivo by generating oxygen with an oxygen generator that electrolyzes water to oxygen and hydrogen. Oxygen can be generated substantially without generating free hydrogen using a multilayer electrolyzer sheet having a proton exchange membrane sandwiched by an anode layer and a cathode layer. The oxygen generator may be used to supply oxygen to cells contained by a culture plate, a culture flask, a microtiter plate or an extracorporeal circuit, or to cells in an encapsulating chamber for implanting in the body such as an immunoisolation chamber bounded by a semipermeable barrier layer that allows selected components to enter and leave the chamber. A bioactive molecule may be present with the cells. Oxygen can be delivered in situ to cells within the body such as by implanting the oxygen generator in proximity to cell-containing microcapsules in an intraperitoneal space, or by implanting a system containing the oxygen generator in proximity to an immunoisolation chamber containing cells. The oxygen generator may be connected to a current control circuit and a power supply.

In U.S. Pat. No. 10,231,817 B2, inventors Tempelman et al., which issued Mar. 19, 2019, and which is incorporated herein by reference in its entirety, there is disclosed a system for gas treatment of a cell implant. According to the aforementioned patent (hereinafter "the '817 patent"), the system enhances the viability and function of cellular implants, particularly those with high cellular density, for use in human or veterinary medicine. The system utilizes a miniaturized electrochemical gas generator subsystem that continuously supplies oxygen and/or hydrogen to cells within an implantable and immunoisolated cell containment subsystem to facilitate cell viability and function at high cellular density while minimizing overall implant size. The cell containment subsystem is equipped with features to allow gas delivery through porous tubing or gas-only permeable internal gas compartments within the implantable cell containment subsystem. Furthermore, the gas generator subsystem includes components that allow access to water for electrolysis while implanted, thereby promoting long-term implantability of the gas generator subsystem. An application of the system is a pancreatic islet (or pancreatic islet analogue) implant for treatment of Type I diabetes (T1D) that would be considered a bio-artificial pancreas.

One shortcoming that has been identified by the present inventors with electrolytic gas generators of the type conventionally used with subdermal implant devices is that many such electrolytic gas generators are configured to port the generated gas axially, i.e., along the longitudinal axis of the electrolytic gas generator. This type of construction may be disadvantageous because it may increase the thickness of the overall subdermal implant device. As can readily be appreciated, it is often desirable to minimize the thickness of a subdermal implant device.

SUMMARY OF THE INVENTION

It is an object of the present invention to provide a novel electrolytic gas generator.

According to one aspect of the invention, there is provided an electrolytic gas generator for electrolyzing a reactant to generate at least a first gas, the electrolytic gas generator comprising (a) a polymer electrolyte membrane, the polymer electrolyte membrane having opposing first and second faces; (b) a first electrode, the first electrode being electrically coupled to the first face of the polymer electrolyte membrane; (c) a second electrode, the second electrode being electrically coupled to the second face of the polymer electrolyte membrane; (d) a first current collector, the first current collector being electrically coupled to the first electrode, wherein the first current collector comprises a first electrically-conductive extension for use in mounting a conductive lead and wherein the first current collector further comprises a gas conduit for porting laterally gas generated at the first electrode; (e) a second current collector, the second current collector being electrically coupled to the second electrode; (f) a current source; (g) a first conductive lead, the first conductive lead electrically coupling the first current collector to the current source, the first conductive lead comprising a first end secured to the first electrically-conductive extension; and (h) a second conductive lead, the second conductive lead electrically coupling the second current collector to the current source.

In a more detailed feature of the invention, the electrolytic gas generator may be a water electrolyzer.

In a more detailed feature of the invention, at least a portion of the gas conduit may pass through at least a portion of the first electrically-conductive extension.

In a more detailed feature of the invention, at least a portion of the gas conduit may pass through the entirety of the first electrically-conductive extension.

In a more detailed feature of the invention, the first current collector may comprise a top member and a bottom member, and the top member and the bottom member may be bonded to one another and may jointly define the gas conduit.

In a more detailed feature of the invention, the first current collector may comprise a top member and a bottom member, and the top member and the bottom member may be bonded to one another and may jointly define the gas conduit and the first electrically-conductive extension.

In a more detailed feature of the invention, the gas conduit may be formed by one or more etchings on at least one of the top member and the bottom member.

In a more detailed feature of the invention, the gas conduit may be formed by one or more etchings on both the top member and the bottom member.

In a more detailed feature of the invention, the gas conduit may be formed by a through hole on the bottom member and an elongated recess on the top member, and the elongated recess may have a first end aligned with the through hole of the bottom member and a second end at the periphery of the top member.

In a more detailed feature of the invention, both the top member and the bottom member may be electrically conductive.

In a more detailed feature of the invention, the bottom member may be electrically conductive and the top member may be electrically-non-conductive.

In a more detailed feature of the invention, the first current collector may further comprise a second electrically-conductive extension for use in mounting a conductive lead.

In a more detailed feature of the invention, the first electrically-conductive extension and the second electrically-conductive extension may be spaced apart from one another by approximately 180 degrees.

In a more detailed feature of the invention, the first electrically-conductive extension may have a proximal portion of comparatively greater width and a distal portion of comparatively lesser width.

In a more detailed feature of the invention, the first electrically-conductive extension may have a substantially uniform width.

In a more detailed feature of the invention, the second current collector may comprise a first electrically-conductive extension for use in mounting a conductive lead, and the second current collector may further comprise a gas conduit for porting laterally gas generated at the second electrode.

In a more detailed feature of the invention, at least a portion of the gas conduit of the second current collector may pass through at least a portion of the second electrically-conductive extension of the second current collector.

In a more detailed feature of the invention, the second current collector may comprise a top member and a bottom member, and the top member and the bottom member may be bonded to one another and may jointly define the gas conduit of the second current collector.

In a more detailed feature of the invention, the second current collector may comprise a top member and a bottom member, the top member and the bottom member may be bonded to one another and may jointly define the gas conduit of the second current collector and the first electrically-conductive extension of the second current collector.

In a more detailed feature of the invention, the electrolytic gas generator may further comprise a diaphragm interposed between the first electrode and the first current collector, the diaphragm may be electrically-conductive and may be reversibly deformable between a first state in which the diaphragm electrically couples the first current collector to the first electrode and a second state in which the first current collector is at least partially disconnected from the first electrode.

In a more detailed feature of the invention, the diaphragm may have an aperture for passage therethrough of gas generated at the first electrode, and the aperture may be positioned proximate to a periphery of the diaphragm in a location that does not electrically contact the first electrode.

According to another aspect of the invention, there is provided an electrolytic gas generator for electrolyzing a reactant to generate at least a first gas, the electrolytic gas generator comprising (a) a polymer electrolyte membrane, the polymer electrolyte membrane having opposing first and second faces; (b) a first electrode, the first electrode being electrically coupled to the first face of the polymer electrolyte membrane; (c) a second electrode, the second electrode being electrically coupled to the second face of the polymer electrolyte membrane; (d) a first current collector assembly, the first current collector assembly comprising (i) a first current collector, wherein the first current collector comprises a first electrically-conductive extension for use in mounting a conductive lead and wherein the first current collector further comprises a gas conduit for porting laterally gas generated at the first electrode, (ii) a frame, the frame being non-electrically-conductive, (iii) a diaphragm, the diaphragm being secured between the first current collector and the frame, the diaphragm being electrically-conductive and being reversibly deformable between a first state in which the first current collector is electrically coupled to the first electrode and a second state in which the first current collector is at least partially electrically disconnected from the first electrode; (e) a second current collector, the second current collector being electrically-conductive and being electrically coupled to the second electrode; (f) a current source; (g) a first conductive lead, the first conductive lead electrically coupling the first current collector to the current source, the first conductive lead comprising a first end secured to the first electrically-conductive extension; and (h) a second conductive lead, the second conductive lead electrically coupling the second current collector to the current source.

In a more detailed feature of the invention, the diaphragm may have an aperture for passage therethrough of gas generated at the first electrode, and the aperture may be positioned proximate to a periphery of the diaphragm in a location that does not electrically contact the first electrode.

In a more detailed feature of the invention, the first current collector may further comprise an annular portion, and the first electrically-conductive extension may extend radially outwardly from the annular portion.

In a more detailed feature of the invention, the annular portion of the first current collector may comprise an annular recess of a bottom surface thereof, an inlet to the gas conduit may be positioned within the annular recess, and the aperture of the diaphragm may be aligned with the annular recess of the first current collector.

In a more detailed feature of the invention, the frame may be annular, the frame may comprise an annular recess on a top surface thereof, the frame may have an aperture, the aperture of the frame may be positioned within the annular recess of the frame, and the annular recess of the frame may be aligned with the aperture of the diaphragm.

In a more detailed feature of the invention, the first current collector may comprise a top member and a bottom member, and the top member and the bottom member may be bonded to one another and may jointly define the gas conduit.

In a more detailed feature of the invention, the first current collector may comprise a top member and a bottom member, the top member and the bottom member may be bonded to one another and may jointly define the gas conduit and the first electrically-conductive extension.

In a more detailed feature of the invention, the electrolytic gas generator may further comprise a resiliently-compressible member engaged with the first current collector to bias the first current collector towards the first state.

It is another object of the present invention to provide a novel current collector.

According to one aspect of the invention, there is provided a current collector for use in an electrolytic gas generator, the current collector comprising (a) a body, the body being electrically conductive; and (b) an extension, the extension extending laterally from the body and comprising an electrically-conductive surface electrically coupled to the body; (c) wherein the body and the extension jointly define a gas conduit having a first end in the body and a second end in the extension.

In a more detailed feature of the invention, the body may be disk-shaped and the extension may extend radially from the body.

In a more detailed feature of the invention, the first end of the gas conduit may terminate in a through hole in the body.

In a more detailed feature of the invention, the first end of the gas conduit may terminate in an opening at a bottom surface of the body.

In a more detailed feature of the invention, the second end of the gas conduit may be disposed at a distal end of the extension.

In a more detailed feature of the invention, the second end of the gas conduit may be spaced proximally a distance from a distal end of the extension.

In a more detailed feature of the invention, the body may be annular, and the extension may extend radially from the body.

In a more detailed feature of the invention, the body and the extension may be formed by joining a top member and a bottom member, and the top member and the bottom member may be bonded to one another and may jointly define the gas conduit.

In a more detailed feature of the invention, the body and the extension may be formed by joining a top member and a bottom member, and the top member and the bottom member may be bonded to one another and may jointly define the gas conduit and the extension.

In a more detailed feature of the invention, the gas conduit may be formed by one or more etchings on at least one of the top member and the bottom member.

In a more detailed feature of the invention, the gas conduit may be formed by one or more etchings on both the top member and the bottom member.

In a more detailed feature of the invention, the body may further comprise one or more pores.

For purposes of the present specification and claims, various relational terms like "top," "bottom," "proximal," "distal," "upper," "lower," "front," and "rear" may be used to describe the present invention when said invention is positioned in or viewed from a given orientation. It is to be understood that, by altering the orientation of the invention, certain relational terms may need to be adjusted accordingly.

Additional objects, as well as aspects, features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. These drawings are not necessarily drawn to scale, and certain components may have undersized and/or oversized dimensions for purposes of explication. In the drawings wherein like reference numeral represent like parts:

FIG. 1 is a top perspective view of a first embodiment of an electrolytic gas generator constructed according to the teachings of the present invention;

FIG. 2 is a bottom perspective view of the electrolytic gas generator of FIG. 1;

FIGS. 5(a) and 5(b) are top perspective and bottom perspective views, respectively, of the anode current collector assembly shown in FIG. 1;

FIGS. 6(a) and 6(b) are enlarged bottom perspective and section views, respectively, of the anode current collector shown in FIG. 5(a);

FIG. 7 is a bottom perspective view of the top member of the anode current collector shown in FIG. 6(a);

FIG. 8 is a top perspective view of the bottom member of the anode current collector shown in FIG. 6(a);

FIG. 11 is a bottom perspective view of the top member of the cathode current collector shown in FIG. 10(a);

FIG. 12 is a top perspective view of the bottom member of the cathode current collector shown in FIG. 10(a);

FIGS. 13(a) and 13(b) are top perspective and bottom perspective views, respectively, of an alternative embodiment of an anode current collector to the anode current collector shown in FIG. 6(a);

FIG. 14 is a top view of the bottom member of the anode current collector shown in FIG. 13(a);

FIG. 15 is a bottom view of the top member of the anode current collector shown in FIG. 13(a);

FIGS. 16(a) and 16(b) are top perspective and bottom perspective views, respectively, of an alternative embodiment of a cathode current collector to the cathode current collector shown in FIG. 10(a);

FIG. 17 is a top view of the bottom member of the cathode current collector shown in FIG. 16(a);

FIG. 18 is a top view of the top member of the cathode current collector shown in FIG. 16(a);

FIG. 19 is a top perspective view of a second embodiment of an electrolytic gas generator constructed according to the teachings of the present invention;

FIG. 20 is a bottom perspective view of the electrolytic gas generator of FIG. 19;

FIG. 24 is a top perspective view of the anode current collector assembly shown in FIG. 21;

FIG. 25 is a section view of the anode current collector assembly of FIG. 24 taken along line 24-24;

FIGS. 27(a), 27(b) and 27(c) are top perspective, bottom perspective, and section views, respectively, of the anode current collector shown in FIG. 24;

FIGS. 29(a) and 29(b) are top perspective and bottom perspective views, respectively, of the bottom member of the anode current collector shown in FIG. 24;

FIGS. 31(a) and 31(b) are top perspective and section views, respectively, of the cathode current collector shown in FIG. 21.

DETAILED DESCRIPTION OF THE INVENTION

The present invention is directed, in part, at a novel electrolytic gas generator and is also directed, in part, at combination electrical lead and gas port terminals for use in an electrolytic gas generator.

According to one embodiment, the present invention enables the implantation of electrolytic gas generators in a thin format that eliminates the need for threaded fittings on an endplate. According to a preferred aspect of the invention, terminals are provided that capture gas and route it laterally through a lumen, which either can be connected directly to a destination or can have tubing attached to it to route the gas elsewhere. The present invention is not limited to implantable devices, but rather, can be applied to any system where horizontal space is limited or system simplification is desired.

According to one feature of the invention, devices are provided for porting of gas and for carrying electrical current. The devices comprise a flow path for gas through a lumen of an electrically conductive material. The electrically conductive material can be etched or otherwise formed to various shapes, depending on the application, and the lumen shape can be changed depending on the desired termination.

Figure 3:
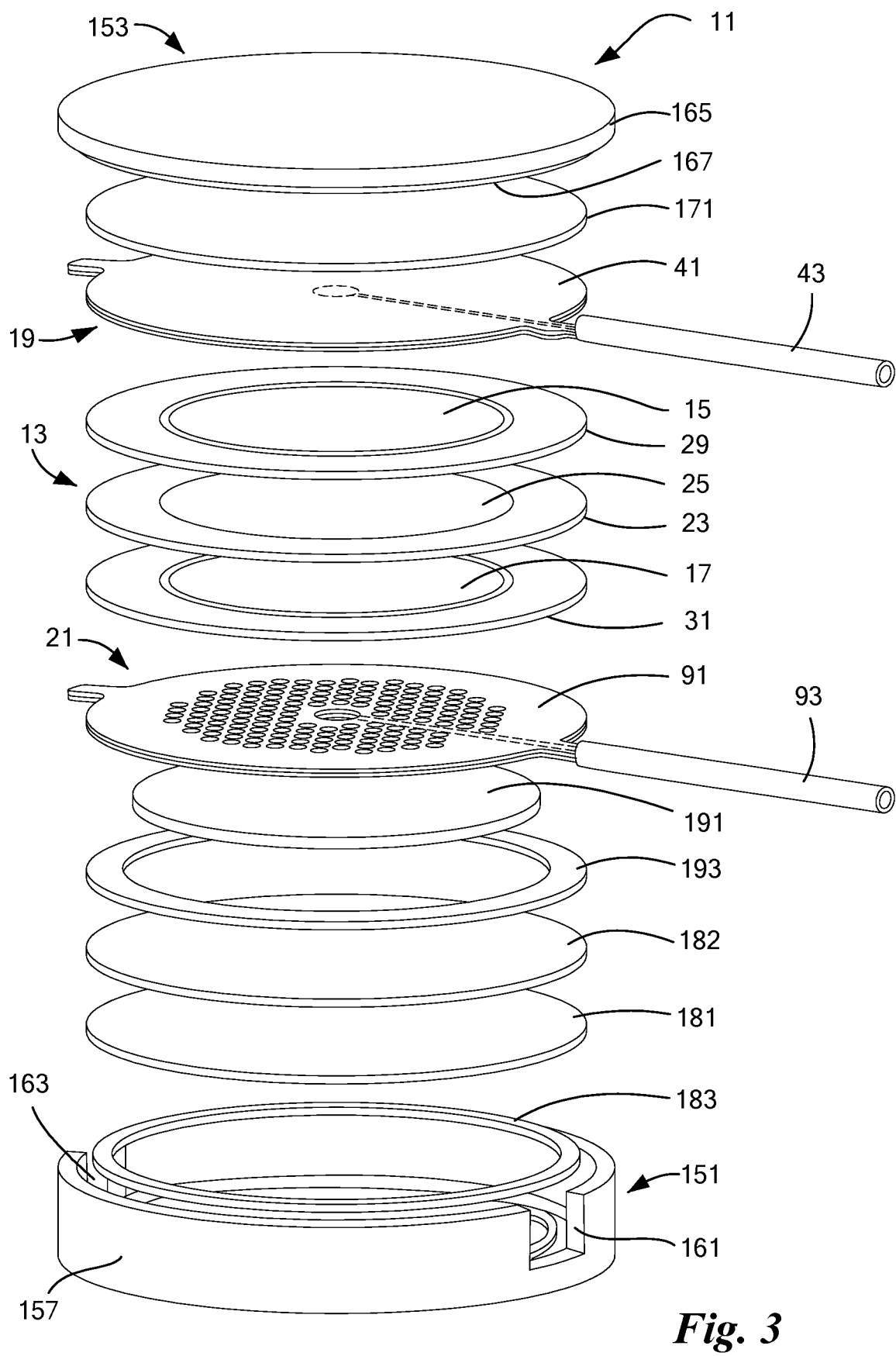
FIG. 3 is a partly exploded perspective view of the electrolytic gas generator of FIG. 1, with certain features of the anode current collector and the cathode current collector that are not otherwise visible being shown in phantom.

Referring now to FIGS. 1 through 3, there are shown various views of a first embodiment of an electrolytic gas generator, the electrolytic gas generator being constructed according to the teachings of the present invention and being represented generally by reference numeral 11. Details of electrolytic gas generator 11 that are discussed elsewhere in this application or that are not critical to an understanding of the invention may be omitted from one or more of FIGS. 1 through 3 or from the accompanying description herein or may be shown in one or more of FIGS. 1 through 3 and/or described herein in a simplified manner. For example, a current source, such as a battery, that may be used to operate electrolytic gas generator 11 is not shown in FIGS. 1 through 3.

Electrolytic gas generator 11, which may be in the form of a water electrolyzer, and, in particular, may be in the form of an implantable water electrolyzer, may comprise a membrane electrode assembly (MEA) 13, an anode support 15, a cathode support 17, an anode current collector assembly 19, and a cathode current collector assembly 21.

Figure 4A:
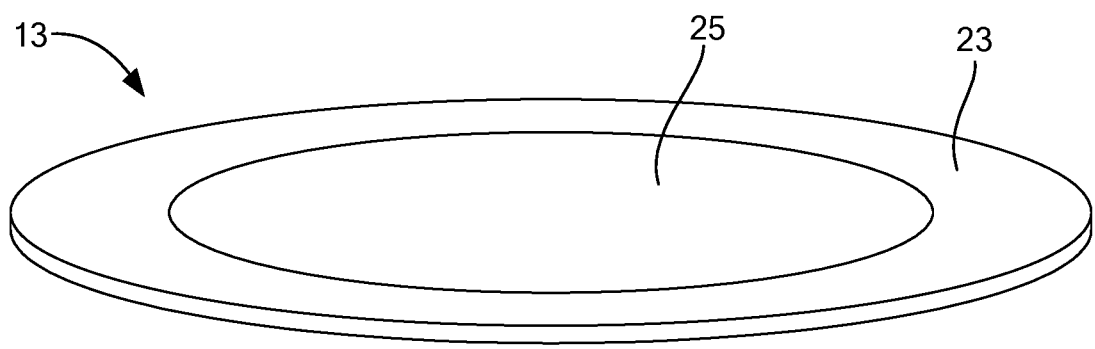
FIGS. 4(a) and 4(b) are top and bottom perspective views, respectively, of the membrane electrode assembly shown in FIG. 3.
Figure 4B:
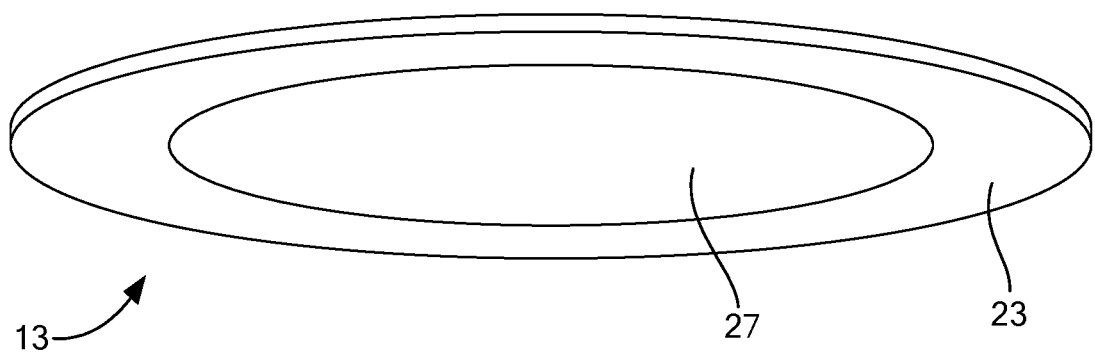

Membrane electrode assembly 13, which is also shown separately in FIGS. 4(a) and 4(b), may comprise a solid polymer electrolyte membrane (PEM) 23. Polymer electrolyte membrane 23 is preferably a non-porous, ionically-conductive, electrically-non-conductive, liquid-permeable and substantially gas-impermeable membrane. Polymer electrolyte membrane 23 may consist of or comprise a homogeneous perfluorosulfonic acid (PFSA) polymer. Said PFSA polymer may be formed by the copolymerization of tetrafluoroethylene and perfluorovinylether sulfonic acid. See e.g., U.S. Pat. No. 3,282,875, inventors Connolly et al., issued Nov. 1, 1966; U.S. Pat. No. 4,470,889, inventors Ezzell et al., issued Sep. 11, 1984; U.S. Pat. No. 4,478,695, inventors Ezzell et al., issued Oct. 23, 1984; and U.S. Pat. No. 6,492,431, inventor Cisar, issued Dec. 10, 2002, all of which are incorporated herein by reference in their entireties. A commercial embodiment of a PFSA polymer electrolyte membrane is manufactured by The Chemours Company FC, LLC (Fayetteville, N.C.) as NAFION™ extrusion cast PFSA polymer membrane.

Polymer electrolyte membrane 23 may be a generally planar unitary structure in the form of a continuous film or sheet. In the present embodiment, when viewed from above or below, polymer electrolyte membrane 23 may have a generally circular shape. Moreover, the overall shape of electrolytic gas generator 11, when viewed from above or below, may correspond generally to the shape of polymer electrolyte membrane 23. However, it is to be understood that polymer electrolyte membrane 23, as well as electrolytic gas generator 11 as a whole, is not limited to a generally circular shape and may have a generally rectangular shape or other suitable shape.

Membrane electrode assembly 13 may further comprise an anode electrocatalyst layer 25 and a cathode electrocatalyst layer 27. Anode electrocatalyst layer 25 may be positioned in direct contact with polymer electrolyte membrane 23 and, in the present embodiment, is shown as being positioned directly above, centered relative to, and in contact with a portion of the top surface of polymer electrolyte membrane 23. Anode electrocatalyst layer 25 defines the electrochemically active area of the anode of electrolytic gas generator 11 and preferably is sufficiently porous and electrically- and ionically-conductive to sustain a high rate of surface oxidation reaction. Anode electrocatalyst layer 25, which may be an anode electrocatalyst layer of the type conventionally used in a PEM-based water electrolyzer, may comprise electrocatalyst particles in the form of a finely divided corrosion-resistant, electrically-conductive (and, optionally, ionically-conductive) material (e.g., a metal powder) which can sustain a high rate of electrochemical reaction. The electrocatalyst particles may be distributed within anode electrocatalyst layer 25 along with a binder, which is preferably ionically-conductive, to provide mechanical fixation.

Cathode electrocatalyst layer 27 may be positioned in direct contact with polymer electrolyte membrane 23 and, in the present embodiment, is shown as being positioned directly below, centered relative to, and in contact with a portion of the bottom surface of polymer electrolyte membrane 23. Cathode electrocatalyst layer 27 defines the electrochemically active area of the cathode of electrolytic gas generator 11 and preferably is sufficiently porous and electrically- and ionically-conductive to sustain a high rate of surface reduction reaction. Cathode electrocatalyst layer 27, which may be a cathode electrocatalyst layer of the type conventionally used in a PEM-based water electrolyzer, may comprise electrocatalyst particles in the form of a finely divided corrosion-resistant, electrically-conductive (and, optionally, ionically-conductive) material (e.g., a metal powder) which can sustain a high rate of electrochemical reaction. The electrocatalyst particles may be distributed within cathode electrocatalyst layer 27 along with a binder, which is preferably ionically-conductive, to provide mechanical fixation.

Anode support 15, which may be an anode support of the type conventionally used in a PEM-based water electrolyzer and may be, for example, a film or sheet of porous titanium (or a similarly suitable, porous, corrosion-resistant electrically-conductive material), may be positioned over and in direct contact with anode electrocatalyst layer 25. Preferably, anode support 15 is sufficiently porous to allow gas to readily diffuse therethrough. To this end, anode support 15 may have pore sizes on the order of, for example, approximately 0.0005-0.5 mm. Anode support 15 may also contain macroscopic channel features, for example, on the order of 0.1-10 mm to further assist in gas diffusion. In addition, anode support 15 is electrically-conductive to provide electrical connectivity between anode electrocatalyst layer 25 and the anode-side current collector to be discussed below, and anode support 15 is also preferably ionically-non-conductive. Anode support 15 may be positioned in direct contact with anode electrocatalyst layer 25 and, in the present embodiment, is shown as being positioned directly on top of anode electrocatalyst layer 25 such that anode electrocatalyst layer 25 may be sandwiched between and in contact with polymer electrolyte membrane 23 and anode support 15. Anode support 15 may be dimensioned to entirely cover anode electrocatalyst layer 25, and anode support 15 preferably is dimensioned to substantially match the footprint of anode electrocatalyst layer 25. In this fashion, anode support 15 and anode electrocatalyst layer 25 may collectively function as the anode of electrolytic gas generator 11. A support gasket 29, which may be made of a made of a flexible, compliant, non-porous material such as rubber, soft plastic, or, for example, fluoroelastomer rubber material, such as VITON® synthetic rubber material (The Chemours Company FC, LLC, Fayetteville, N.C.), may peripherally surround, fluidically seal, and electrically insulate anode support 15. Preferably, support gasket 29 is dimensioned so that its periphery substantially matches the periphery of polymer exchange membrane 23.

Cathode support 17, which may be a cathode support of the type conventionally used in a PEM-based water electrolyzer and may be, for example, a film or sheet of porous carbon (or a similarly suitable, porous, corrosion-resistant, electrically-conductive material), may be positioned under and in direct contact with cathode electrocatalyst layer 27. Preferably, cathode support 17 is sufficiently porous to allow gas to readily diffuse therethrough. To this end, cathode support 17 may have pore sizes on the order of, for example, approximately 0.005-0.5 mm. Cathode support 17 may also contain macroscopic channel features, for example, on the order of 0.1-10 mm to further assist in gas diffusion. In addition, cathode support 17 is electrically-conductive to provide electrical connectivity between cathode electrocatalyst layer 27 and the cathode-side current collector to be discussed below, and cathode support 17 is also preferably ionically-non-conductive. Cathode support 17 may be positioned in direct contact with cathode electrocatalyst layer 27 and, in the present embodiment, is shown as being positioned directly below and in contact with cathode electrocatalyst layer 27 such that cathode electrocatalyst layer 27 may be sandwiched between and in contact with polymer electrolyte membrane 23 and cathode support 17. Cathode support 17 may be dimensioned to entirely cover cathode electrocatalyst layer 27, and cathode support 17 preferably is dimensioned to substantially match the footprint of cathode electrocatalyst layer 27. In this fashion, cathode support 17 and cathode electrocatalyst layer 27 may collectively function as the cathode of electrolytic gas generator 11. A support gasket 31, which may be made of a flexible, compliant, non-porous material such as rubber, soft plastic, or, for example, fluoroelastomer rubber material, may peripherally surround, fluidically seal, and electrically insulate cathode support 17. Preferably, support gasket 31 is dimensioned so that its periphery substantially matches the periphery of polymer exchange membrane 23.

Anode current collector assembly 19, which is also shown separately in FIGS. 5(a) and 5(b), may comprise an anode current collector 41 and a length of tubing 43.

Anode current collector 41, which is also shown separately in FIGS. 6(a) and 6(b), may be positioned over and in direct contact with anode support 15 and support gasket 29. As will be discussed further below, anode current collector 41 may be constructed to perform two different functions, namely, (1) to conduct current from anode support 15 to an electrically conductive lead 45 (shown in phantom in FIG. 5(a)) conductively mounted (e.g., by soldering) on anode current collector 41 and (2) to conduct gas (e.g., $O_2$) that is generated at anode electrocatalyst layer 25 and passed through anode support 15 along to tubing 43.

In the present embodiment, anode current collector 41 may be shaped to include a disk portion 47. Disk portion 47, which may be dimensioned to substantially match the combined footprints of anode support 15 and support gasket 29, may be shaped to include an inlet 49. Inlet 49, which may be used to receive gas (e.g., $O_2$) generated at the anode of electrolytic gas generator 11, may be accessible from a bottom surface of disk portion 47. In the present embodiment, inlet 49 is shown as being centrally located in disk portion 47; however, inlet 49 need not be centrally located, but rather, need only be positioned over some portion of anode support 15.

Anode current collector 41 may be further shaped to include a first extension 53. First extension 53 may extend radially outwardly from disk portion 47 for a distance. In the present embodiment, first extension 53 may be shaped to include a proximal portion 55 of comparatively greater width and a distal portion 57 of comparatively lesser width. In this manner, tubing 43 may be coaxially mounted over distal portion 57 of first extension 53, and conductive lead 45, which may be electrically coupled to a battery or similarly suitable current source, may be mounted on proximal portion 55 of first extension 53. In other words, distal portion 57 of first extension 53 may serve as a fitting for receiving tubing 43, and proximal portion 55 of first extension 53 may serve as a contact surface for conductive lead 45. If desired, conductive lead 45 may be mounted on proximal portion 55 so as to be oriented generally parallel to tubing 43; however, such a parallel orientation is not required. Also, it is to be understood that first extension 53 need not have portions of different widths and, instead, may have a constant width over its entire length.

A lumen 59 may be provided in anode current collector 41 and may extend continuously from inlet 49 to a distal end 61 of first extension 53, lumen 59 terminating at distal end 61 in an outlet 63. In this manner, as will be discussed further below, a gas, such as oxygen, that is generated at the anode of electrolytic gas generator 11 may enter anode current collector 41 through inlet 49 and may travel through lumen 59, exiting at outlet 63. Thus, the fluid path spanning from inlet 49 to outlet 63 serves as a gas conduit to port gas laterally through anode current collector 41.

Anode current collector 41 may be further shaped to include a second extension 65. Second extension 65 may extend radially outwardly from disk portion 47 for a distance and may serve as an alternative location for mounting conductive lead 45. In the present embodiment, first extension 53 and second extension 65 may be spaced apart from one another around the periphery of disk portion 47 by an angle of approximately 180 degrees. Such spacing may be desirable where, for example, one wishes to orient anode current collector assembly 19 and cathode current collector assembly 21 relative to one another by an angle of 180 degrees and yet have conductive leads extending in substantially the same direction. Such spacing may also be desirable where one wishes to orient anode current collector assembly 19 and cathode current collector assembly 21 in substantially the same direction, as in the case of the present embodiment, but wishes to have the conductive leads extend in opposite directions. As can be appreciated, where such capabilities are not desired, second extension 65 may be omitted.

In the present embodiment, anode current collector 41 may be formed by the joinder of a top member 71 and a bottom member 73, wherein top member 71 and bottom member 73 have substantially matching footprints. (However, alternatively, anode current collector 41 could be fashioned from a single piece of material.) Top member 71, which is also shown separately in FIG. 7, may be shaped to include a bottom surface 75 having a first recess 77 of circular shape, and bottom member 73, which is also shown separately in FIG. 8, may be shaped to include a correspondingly dimensioned and positioned through hole 79. In this manner, recess 77 and through hole 79, which are aligned, may jointly define inlet 49. Bottom surface 75 of top member 71 may be further shaped to include a radial groove or recess 81 extending from recess 77 to a distal end 83 of a tab 85, wherein groove 81 and bottom member 73 may jointly define lumen 59. Although, in the present embodiment, top member 71 includes groove 81 and bottom member 73 does not include a feature similar to groove 81, it is to be understood that either one or both of top member 71 and bottom member 73 may include a feature similar to groove 81 for use in forming a lumen.

In the present embodiment, each of top member 71 and bottom member 73 may be a rigid, electrically-conductive plate. Examples of materials suitable for use as top member 71 and/or bottom member 73 may include various conductive and corrosion-resistant metals, such as titanium, niobium, and zirconium. Other examples may include electrically-conductive polymers or polymers in which electrically-conductive particles are dispersed. Where top member 71 and bottom member 73 are formed of titanium or a similarly conductive and corrosion-resistant material, top member 71 and bottom member 73 may be joined by diffusion bonding or by any other suitable technique. In addition, where top member 71 and bottom member 73 are formed of titanium or a similarly conductive and corrosion-resistant material, recess 77, through hole 79 and groove 81 may be formed by etching (e.g., photoetching, chemical etching) or by any other suitable technique. Preferably, each of top member 71 and bottom member 73 is made of a material that is non-porous and substantially gas-impermeable. In this manner, substantially all gas conducted through anode current collector 41 may enter through inlet 49, may travel through lumen 59, and may exit through outlet 63.

Although both top member 71 and bottom member 73 may be electrically conductive, one could make bottom member 73 from an electrically-conductive material and could make top member 71 from an electrically-non-conductive material. However, in such a case, conductive lead 45 should be mounted on bottom member 73.

Tubing 43 may comprise a cylindrical tube made of a polymer, such as polyether ether ketone (PEEK), or any other suitable material that is preferably gas-impermeable or of very limited gas-permeability. It is to be understood that, although tubing 43 is mounted over extension 53 in the present embodiment, one could insert tubing 43 into lumen 59.

Figure 9A:
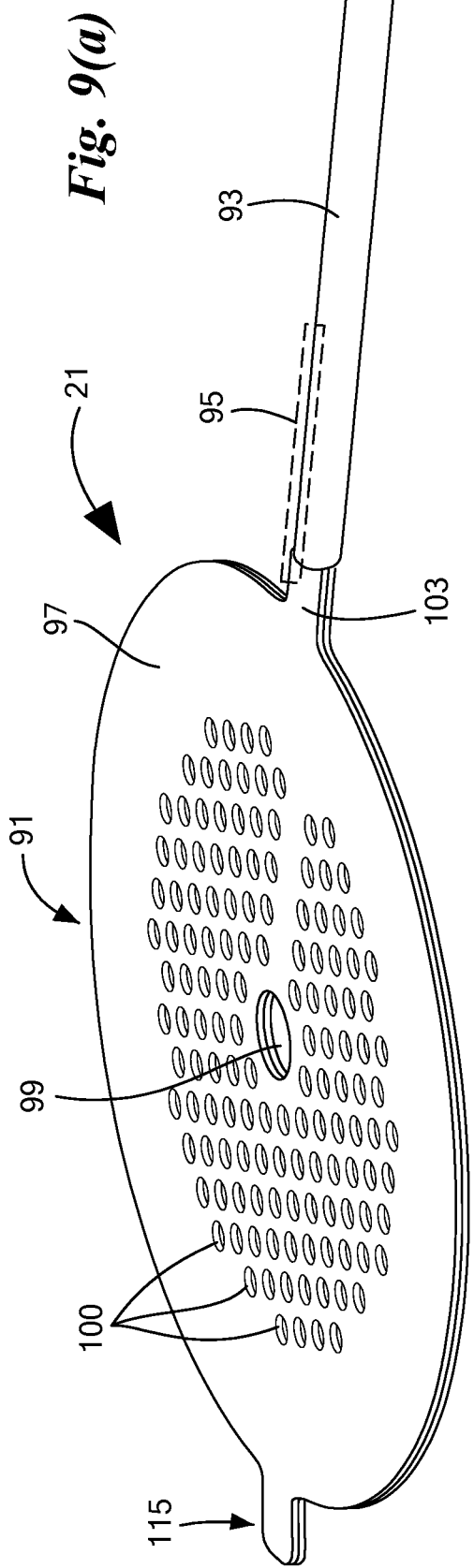
FIGS. 9(a) and 9(b) are top perspective and bottom perspective views, respectively, of the cathode current collector assembly shown in FIG. 1.
Figure 9B:
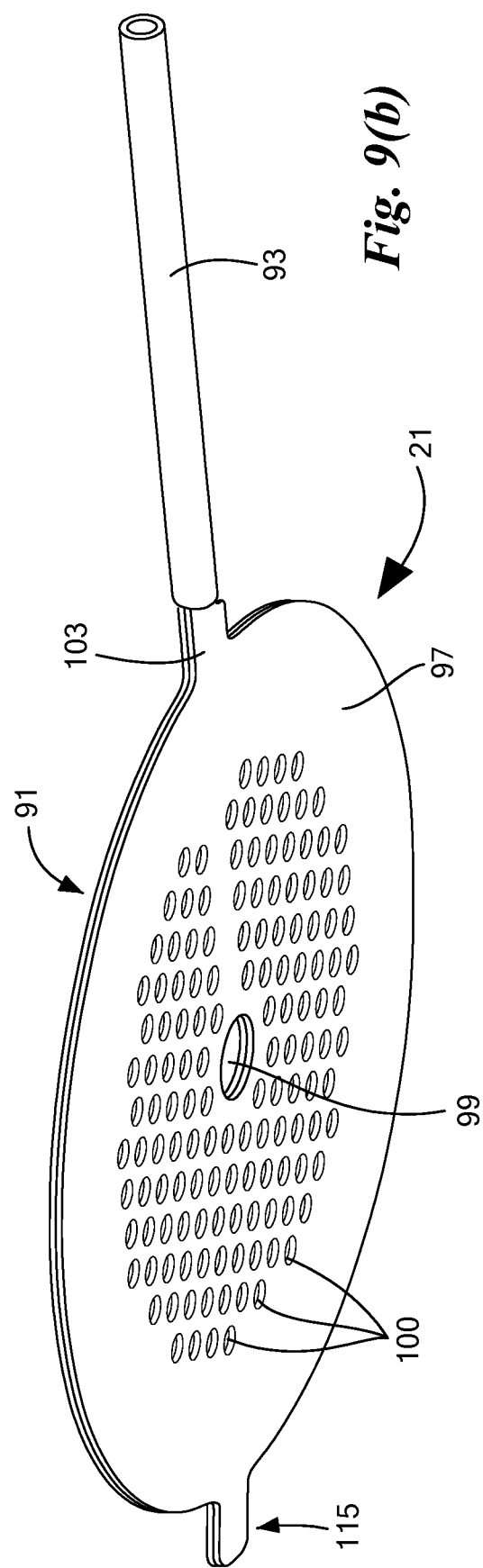

Cathode current collector assembly 21, which is also shown separately in FIGS. 9(a) and 9(b), may comprise a cathode current collector 91 and a length of tubing 93.

Figure 10A:
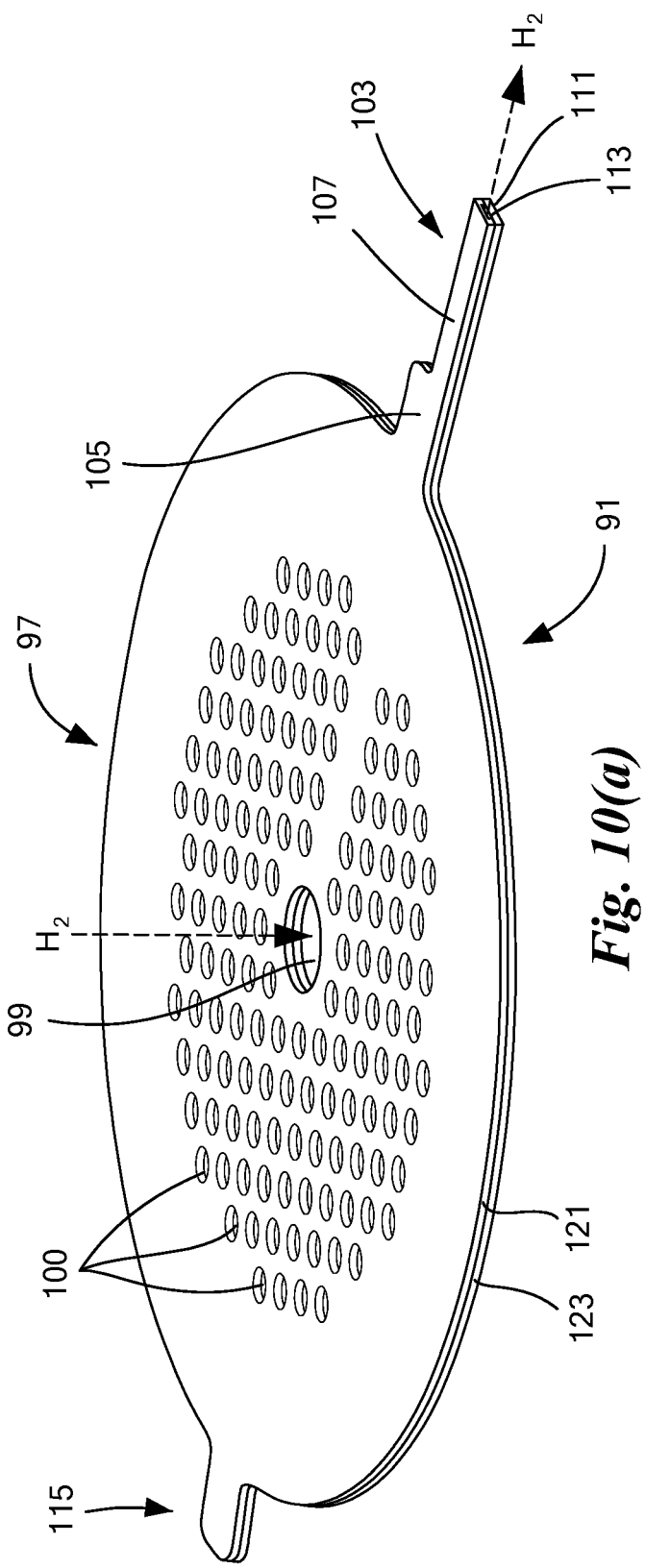
FIGS. 10(a) and 10(b) are enlarged top perspective and section views, respectively, of the cathode current collector shown in FIG. 9(a)
Figure 10B:
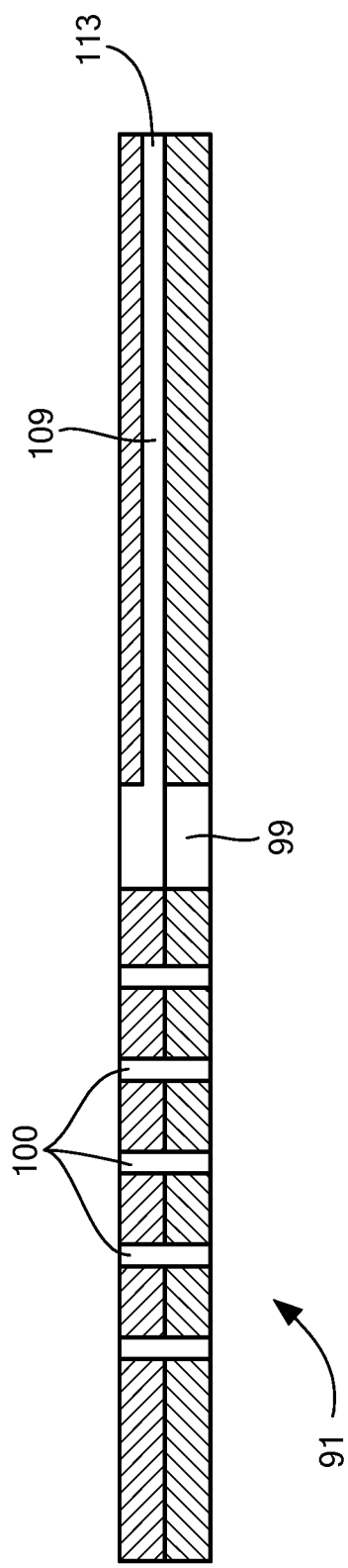

Cathode current collector 91, which is also shown separately in FIGS. 10(a) and 10(b), may be positioned below and in direct contact with cathode support 17 and support gasket 31. As will be discussed further below, cathode current collector 91 may be constructed to perform two different functions, namely, (1) to conduct current from cathode support 17 to an electrically conductive lead 95 (shown in phantom in FIG. 9(a)) conductively mounted (e.g., by soldering) on cathode current collector 91 and (2) to conduct gas (e.g., $H_2$) that is generated at cathode electrocatalyst layer 27 and passed through cathode support 17 along to tubing 93.

In the present embodiment, cathode current collector 91 may be similar in many respects to anode current collector 41. As such, cathode current collector 91 may be shaped to include a disk portion 97. Disk portion 97, which may be dimensioned to substantially match the combined footprints of cathode support 17 and support gasket 31, may be shaped to include an inlet 99. Inlet 99 may be used to receive gas generated at the cathode of electrolytic gas generator 11. In the present embodiment, inlet 99 is shown as a through hole extending entirely through the thickness of disk portion 47; however, it is to be understood that inlet 99 need not be a through hole and, alternatively, could be an opening extending only partially through the thickness of disk portion 97 from a top surface of disk portion 97. Also, in the present embodiment, inlet 99 is shown as being centrally located in disk portion 97; however, inlet 99 need not be centrally located, but rather, need only be positioned over some portion of cathode support 17.

Disk portion 97 may also be shaped to include a plurality of pores 100 extending entirely through the thickness of disk portion 97. Pores 100 may be used to allow water vapor to pass upwardly therethrough to be delivered to MEA 13 to be electrolyzed.

Cathode current collector 91 may be further shaped to include a first extension 103. First extension 103 may extend radially outwardly from disk portion 97 for a distance. In the present embodiment, first extension 103 may be shaped to include a proximal portion 105 of comparatively greater width and a distal portion 107 of comparatively lesser width. In this manner, tubing 93 may be coaxially mounted over distal portion 107 of first extension 103 for purposes to become apparent below, and conductive lead 95, which may be electrically coupled to a battery (such as the opposite terminal of the same battery to which conductive lead 45 is electrically coupled) or another similarly suitable current source, may be mounted on proximal portion 105 of first extension 103. In other words, distal portion 107 of first extension 103 may serve as a fitting for receiving tubing 93, and proximal portion 105 of first extension 103 may serve as a contact surface for conductive lead 95. If desired, conductive lead 95 may be mounted on proximal portion 105 so as to be oriented generally parallel to tubing 93; however, such a parallel orientation is not required. Also, it is to be understood that first extension 103 need not have portions of different widths and, instead, may have a constant width over its entire length.

A lumen 109 may be provided in cathode current collector 91 and may extend continuously from inlet 99 to a distal end 111 of first extension 103, lumen 109 terminating at distal end 111 in an outlet 113. In this manner, as will be discussed further below, a gas, such as hydrogen, that is generated at the cathode of electrolytic gas generator 11 may enter cathode current collector 91 through inlet 99 and may travel through lumen 109, exiting at outlet 113. Thus, the fluid path spanning from inlet 99 to outlet 113 serves as a gas conduit to port gas laterally through cathode current collector 91.

Cathode current collector 91 may be further shaped to include a second extension 115. Second extension may extend radially outwardly from disk portion 97 for a distance and may serve as an alternative location for mounting conductive lead 95. In the present embodiment, first extension 103 and second extension 115 may be spaced apart from one another around the periphery of disk portion 97 by an angle of approximately 180 degrees. Such spacing may be desirable where, for example, one wishes to orient cathode current collector assembly 21 and anode current collector assembly 19 relative to one another by an angle of 180 degrees and yet have conductive leads extend in substantially the same direction. Such spacing may also be desirable where one wishes to orient cathode current collector assembly 21 and anode current collector assembly 19 in substantially the same direction, as in the case of the present embodiment, but wishes to have the conductive leads extend in opposite directions. As can be appreciated, where such capabilities are not desired, second extension 115 may be omitted.

In the present embodiment, cathode current collector 91 may be formed by the joinder of a top member 121 and a bottom member 123, wherein top member 121 and bottom member 123 have substantially matching footprints. (However, alternatively, cathode current collector 91 could be fashioned from a single piece of material.) Top member 121, which is also shown separately in FIG. 11, may be shaped to include a large through hole 127 and a series of small through holes 128, and bottom member 123, which is also shown separately in FIG. 12, may be shaped to include a large through hole 129 and a series of small through holes 130. In this manner, through hole 127 and through hole 129, which are aligned, may jointly define inlet 99, and small through holes 128 and small through holes 130, which are aligned, may jointly define pores 100. A bottom surface 132 of top member 121 may be further shaped to include a radial groove or recess 133 extending from through hole 127 to a distal end 134 of a tab 135, wherein groove 133 and bottom member 123 jointly define lumen 109. Although, in the present embodiment, top member 121 includes groove 133 and bottom member 123 does not include a feature similar to groove 133, it is to be understood that either one or both of top member 121 and bottom member 123 may include a feature similar to groove 133 for use in forming a lumen.

In the present embodiment, each of top member 121 and bottom member 123 may be a rigid, electrically-conductive plate. Examples of materials suitable for use as top member 121 and/or bottom member 123 may include various conductive and corrosion-resistant metals, such as titanium, niobium, and zirconium. Other examples may include electrically-conductive polymers or polymers in which electrically-conductive particles are dispersed. Where top member 121 and bottom member 123 are formed of titanium or a similarly conductive and corrosion-resistant material, top member 121 and bottom member 123 may be joined by diffusion bonding or by any other suitable technique. In addition, where top member 121 and bottom member 123 are formed of titanium or a similarly conductive and corrosion-resistant material, through holes 127, 128, 129, and 130 and groove 133 may be formed by etching (e.g., photoetching, chemical etching) or by any other suitable technique. Preferably, each of top member 121 and bottom member 123 is made of a material that is non-porous and substantially gas-impermeable. In this manner, substantially all gas conducted through cathode current collector 91 may enter through inlet 99, may travel through lumen 99, and may exit through outlet 113.

Although both top member 121 and bottom member 123 may be electrically conductive, one could make top member 121 from an electrically-conductive material and could make bottom member 123 from an electrically-non-conductive material. However, in such a case, conductive lead 95 should be mounted on top member 121.

Tubing 93 may comprise a cylindrical tube made of a polymer, such as polyether ether ketone (PEEK), or any other suitable material that is preferably gas-impermeable or of very limited gas-permeability. It is to be understood that, although tubing 93 is mounted over extension 103 in the present embodiment, one could insert tubing 93 into lumen 109.

Electrolytic gas generator 11 may further comprise a housing base 151 and a housing cover 153, housing base 151 and housing cover 153 jointly defining a housing that may be used to hold many of the other components of electrolytic gas generator 11. Housing base 151, which may be a unitary structure made of a rigid, durable material, may be shaped to include a bottom wall 155, a side wall 157, and an open top. Bottom wall 155 may be shaped to include one or more openings 159 designed to allow a fluid, such as liquid water, to enter into the interior of housing. Side wall 157 may be shaped to include a first opening 161 designed to allow extensions 53 and 103 to pass therethrough and may also be shaped to include a second opening 163 designed to allow extensions 65 and 115 to pass therethrough. Housing cover 153, which may be a unitary structure made of a rigid, durable material, may be shaped to include a top portion 165 and a bottom portion 167. Top portion 165 may be shaped to substantially match the footprint of housing base 151 and may have a bottom surface designed to sit directly on top of the top surface of side wall 157. Bottom portion 167 may be shaped to have a footprint that substantially matches the inner diameter of housing base 151 and may be used to help compress the components stacked within the housing. In this manner, housing base 151 and housing cover 153 not only function to provide a housing for the components of electrolytic gas generator 11 but also function as endplates.

Housing base 151 is preferably made of an electrically-non-conductive material. Housing cover 153 may be made of an electrically-conductive material or an electrically-non-conductive material. Where housing cover 153 is made of an electrically-conductive material, as in the present embodiment, electrolytic gas generator 11 may additionally comprise an electric insulator 171 to electrically insulate housing cover 153 from anode current collector assembly 19.

Electrolytic gas generator 11 may further comprise water-control membranes 181 and 182. Water-control membranes 181 and 182 may be positioned between cathode current collector assembly 21 and bottom wall 155 of housing base 151. In the present embodiment, water-control membrane 181 may be a biocompatible membrane that prevents biofouling in order to promote a stable and consistent water vapor source. An example of a material that may be suitable for use as water-control membrane 181 is expanded PTFE with at least some of the pores being 3 µm or greater in diameter and a preferred thickness range of 30-50 µm. Water-control membrane 182, which may be positioned directly over water-control membrane 181, may be in the form of a vapor transport membrane. Examples of materials suitable for use as water-control membrane 182 may include, but are not limited to, ZITEX® porous polytetrafluoroethylene, GORE-TEX® expanded polytetrafluoroethylene, silicone rubber, PTFE, and TEFLON® polytetrafluoroethylene. An O-ring 183 may be positioned between water-control membrane 181 and bottom wall 155 of housing 151.

Electrolytic gas generator 11 may further comprise a gas diffusion layer 191. Gas diffusion layer 191, which may be made of carbon paper or a similar material, may be positioned between water-control membrane 182 and cathode current collector assembly 21. A gasket 193, which may be made of a flexible, compliant, non-porous material such as rubber or soft plastic, may peripherally surround, fluidically seal, and electrically insulate gas diffusion layer 191.

In use, electrolytic gas generator 11 may be placed in an environment where water is present (such as, but not limited to, at an appropriate location within the body of a person or a non-human animal), and conductive leads 45 and 95 may be coupled to a battery or similar source of current (which may also be, but need not be, within the body of a person or a non-human animal). Water may enter the housing through openings 159 and, to the extent such water is in liquid form, such water may pass through water-control membranes 181 and 182 as water vapor. The water vapor may then pass through gas diffusion layer 191, then through pores 100 (as well as through inlet 99), and then may reach membrane electrode assembly 13, whereupon the water vapor may be electrolyzed to produce oxygen gas at anode electrocatalyst layer 25 and hydrogen gas at cathode electrocatalyst layer 27. The oxygen gas produced at anode electrocatalyst layer 25 may pass through anode support 15 and then may enter lumen 59 of anode current collector 41 through inlet 49. The oxygen gas may then exit lumen 59 through outlet 63 and may be conducted away using tubing 43. In this manner, where, for example, the distal end of tubing 43 is coupled to an implanted cell capsule or the like, oxygen gas may be supplied to the cell capsule. The hydrogen gas produced at cathode electrocatalyst layer 27 may pass through cathode support 17 and then may enter lumen 109 of cathode current collector 91 through inlet 99. (To the extent that some hydrogen gas may pass entirely through the thickness of cathode current collector 91, via pores 100 and/or via inlet 99, is of no consequence.) The hydrogen gas may then exit lumen 109 of cathode current collector 91 through outlet 113 and may be conducted away using tubing 93. The distal end of tubing 93 may be placed near native vasculature so that the hydrogen gas may be expelled during exhalation or may be coupled to a gas diffusion device of the type disclosed in U.S. Patent Application Publication No. US 2018/0318566 A1, inventors Ferrante et al., published Nov. 8, 2018, and U.S. Patent Application Publication No. US 2018/0133383 A1, inventors Ferrante et al., published May 17, 2018, both of which are incorporated herein by reference in their entireties, and may be expelled in accordance with the teachings therein.

As can be appreciated, one advantage of electrolytic gas generator 11, as compared to conventional gas generators, is its low-profile design, due, in part, to the fact that the generated gases may be conducted away radially, as opposed to being conducted away axially, and due, in part, to the fact that separate components for coupling leads and for conducting gases may be eliminated. Moreover, electrolytic gas generator 11 does not require a complicated manifold system for porting the generated gases. Furthermore, electrolytic gas generator 11 enables facile coupling of conductive leads to its current collectors.

Referring now to FIGS. 13(a) and 13(b), there are shown various views of an alternative embodiment of an anode current collector to anode current collector 41, the alternative anode current collector being constructed according to the teachings of the present invention and being represented generally by reference numeral 201.

Anode current collector 201 may be similar in many respects to anode current collector 41. One difference between anode current collector 201 and anode current collector 41 may be that, whereas anode current collector 41 may comprise a first extension 53, anode current collector 201 may instead comprise a first extension 203. First extension 203 may be similar in many respects to first extension 53. However, one difference between first extension 203 and first extension 53 may be that first extension 203 may comprise a recess 205 in a proximal portion 207. Recess 205 may be used to receive one end of a conductive lead or wire to facilitate the soldering or other securing of the conductive lead or wire to proximal portion 207. Another difference between first extension 203 and first extension 53 may be that, whereas first extension 53 may comprise a distal portion 57 that may be uniform in shape and that may terminate in an outlet 63, first extension 203 may comprise a distal portion 209 that may include a disk-shaped portion 211 spaced a short distance proximally from its distal end 213, which distal end 213 may be open or closed. Disk-shaped portion 211 may be shaped to include an upwardly-facing outlet 215, which may be in fluid communication with a lumen 217 leading from an inlet 219. Consequently, an O-ring (not shown) or other similar sealing device may be mounted on disk-shaped portion 211 around outlet 215, and, under the influence of compression, provide a seal for fluid communication to an adjoining fluidic element, such as a tube fitting or manifold (neither shown). Alternatively, a length of tubing (not shown), such as an L-shaped length of tubing of very limited or no gas permeability, may be inserted into complementary outlet 215 or coaxially mounted over distal end 213 if said distal end 213 is open.

Like anode current collector 41, anode current collector 201 may be formed by joining together two members. Referring now to FIGS. 14 and 15, there are shown a top view of a bottom member 221 and a bottom view of a top member 223, respectively, that may be used to form anode current collector 201.

Referring now to FIGS. 16(a) and 16(b), there are shown various views of an alternative embodiment of a cathode current collector to cathode current collector 91, the alternative cathode current collector being constructed according to the teachings of the present invention and being represented generally by reference numeral 251.

Cathode current collector 251 may be similar in many respects to cathode current collector 91. One difference between cathode current collector 251 and cathode current collector 91 may be that, whereas cathode current collector 91 may comprise a first extension 103, cathode current collector 251 may instead comprise a first extension 253. First extension 253 may be similar in many respects to first extension 103. However, one difference between first extension 253 and first extension 103 may be that first extension 253 may comprise a recess 255 in a proximal portion 257. Recess 255 may be used to receive one end of a conductive lead or wire to facilitate the soldering or other securing of the conductive lead or wire to proximal portion 257. Another difference between first extension 253 and first extension 103 may be that, whereas first extension 103 may comprise a distal portion 107 that may be uniform in shape and that may terminate in an outlet 113, first extension 253 may comprise a distal portion 259 that may include a disk-shaped portion 261 spaced a short distance proximally from its distal end 263, which distal end 263 may be open or closed. Disk-shaped portion 261 may be shaped to include an upwardly-facing outlet 265, which may be in fluid communication with a lumen 267 leading from an inlet 269. Consequently, an O-ring (not shown) or other similar sealing device may be mounted on disk-shaped portion 261 around outlet 265, and, under the influence of compression, provide a seal for fluid communication to an adjoining fluidic element, such as a tube fitting or manifold (neither shown). Alternatively, a length of tubing (not shown), such as an L-shaped length of tubing of very limited or no gas permeability, may be inserted into complementary outlet 265 or coaxially mounted over distal end 263 if said distal end 263 is open.

Like cathode current collector 91, cathode current collector 251 may be formed by joining together two members. Referring now to FIGS. 17 and 18, there are shown a top view of a bottom member 271 and a bottom view of a top member 273, respectively, that may be used to form cathode current collector 251.

Figure 21:
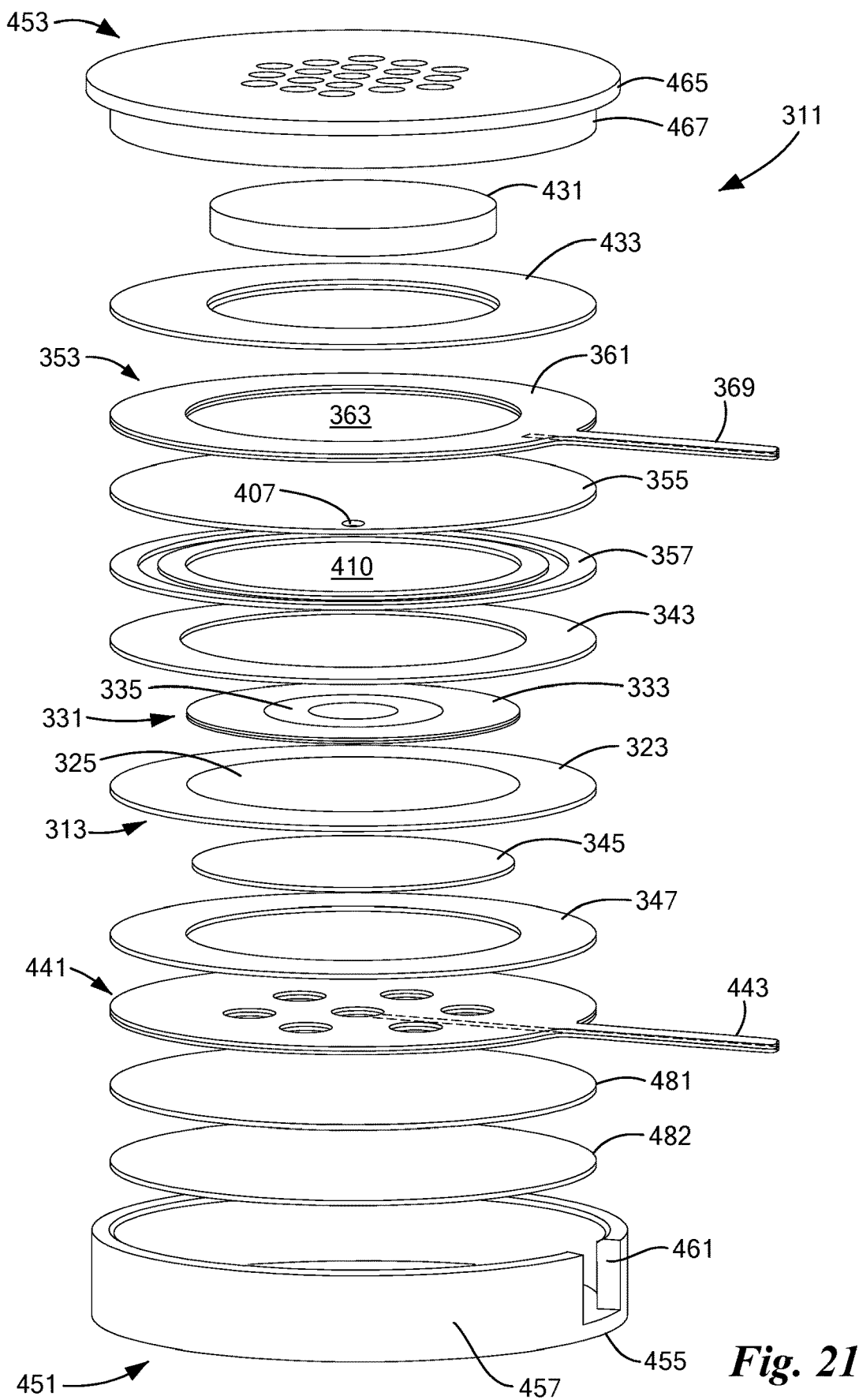
FIG. 21 is a partly exploded perspective view of the electrolytic gas generator of FIG. 19, with certain features of the anode current collector and the cathode current collector that are not otherwise visible being shown in phantom.

Referring now to FIGS. 19 through 21, there are shown various views of a second embodiment of an electrolytic gas generator, the electrolytic gas generator being constructed according to the teachings of the present invention and being represented generally by reference numeral 311. Details of electrolytic gas generator 311 that are discussed elsewhere in this application or that are not critical to an understanding of the invention may be omitted from one or more of FIGS. 19 through 21 or from the accompanying description herein or may be shown in one or more of FIGS. 19 through 21 and/or described herein in a simplified manner. For example, the lengths of tubing for conducting gas from the anode and cathode current collectors are not shown in FIGS. 19 through 21 nor are shown the conductive leads and current source used to operate electrolytic gas generator 311.

Electrolytic gas generator 311, which may be in the form of a water electrolyzer, and, in particular, may be in the form of an implantable water electrolyzer, may comprise a membrane electrode assembly (MEA) 313.

Membrane electrode assembly 313 may be identical to membrane electrode assembly 13 of electrolytic gas generator 11 and may comprise a polymer electrolyte membrane 323, an anode electrocatalyst layer 325 on one face of polymer electrolyte membrane 323, and a cathode electrocatalyst layer (not shown) on an opposing face of polymer electrolyte membrane 323. In the present embodiment, when viewed from above or below, polymer electrolyte membrane 323 may have a generally circular shape. Moreover, the overall shape of electrolytic gas generator 311, when viewed from above or below, may correspond generally to the shape of polymer electrolyte membrane 323. However, it is to be understood that polymer electrolyte membrane 323, as well as electrolytic gas generator 311 as a whole, is not limited to a generally circular shape and may have a generally rectangular shape or other suitable shape.

Figure 22:
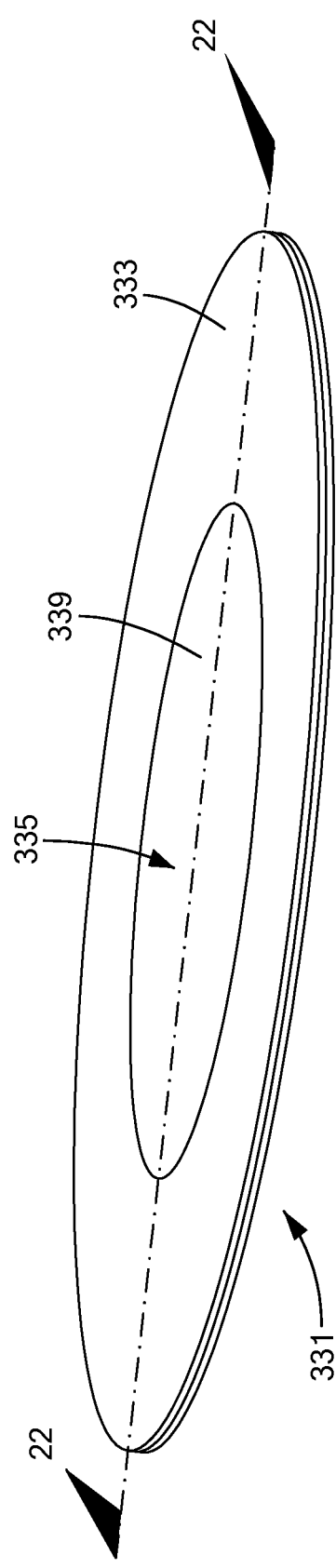
FIG. 22 is an enlarged perspective view of the anode support assembly shown in FIG. 21.
Figure 23:
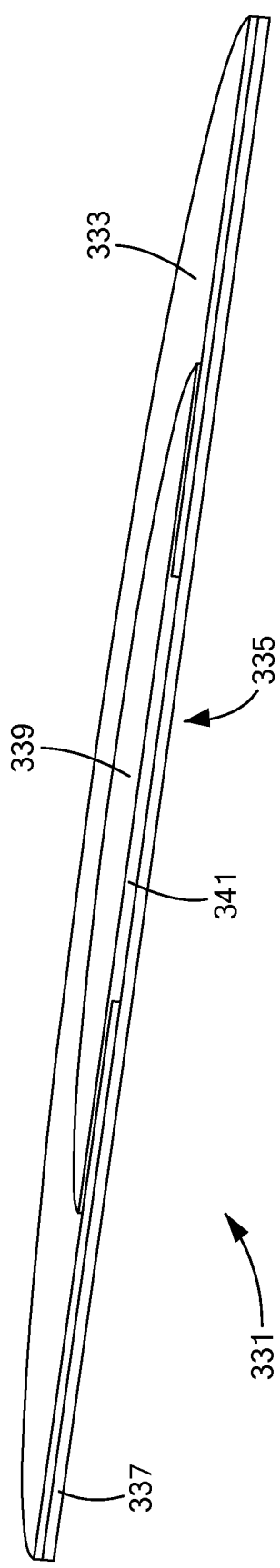
FIG. 23 is a section view of the anode support assembly of FIG. 22 taken along line 22-22.
Figure 26A:
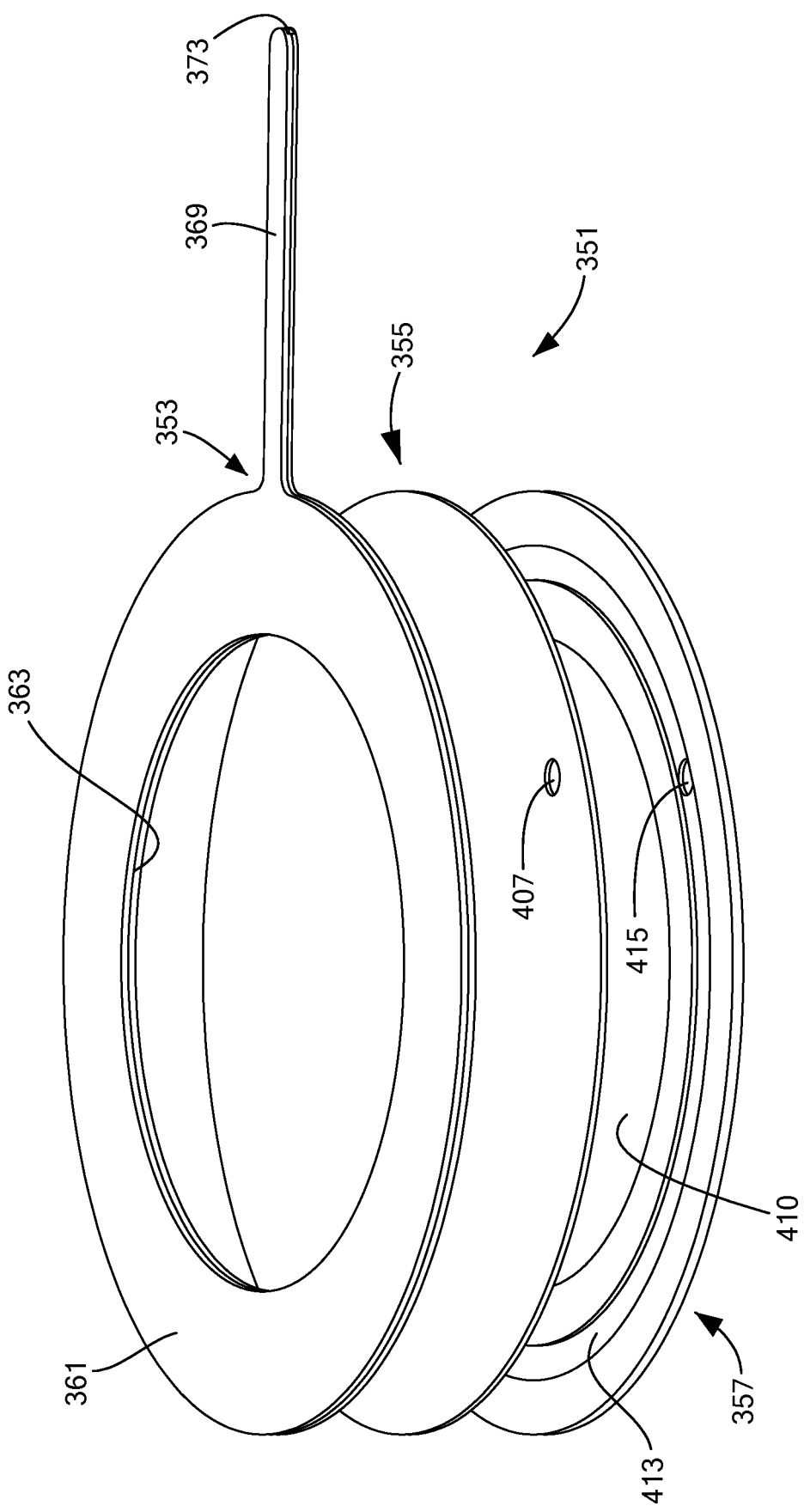
FIGS. 26(a) and 26(b) are partly exploded top perspective and partly exploded bottom perspective views, respectively, of the anode current collector assembly shown in FIG. 24.
Figure 26B:
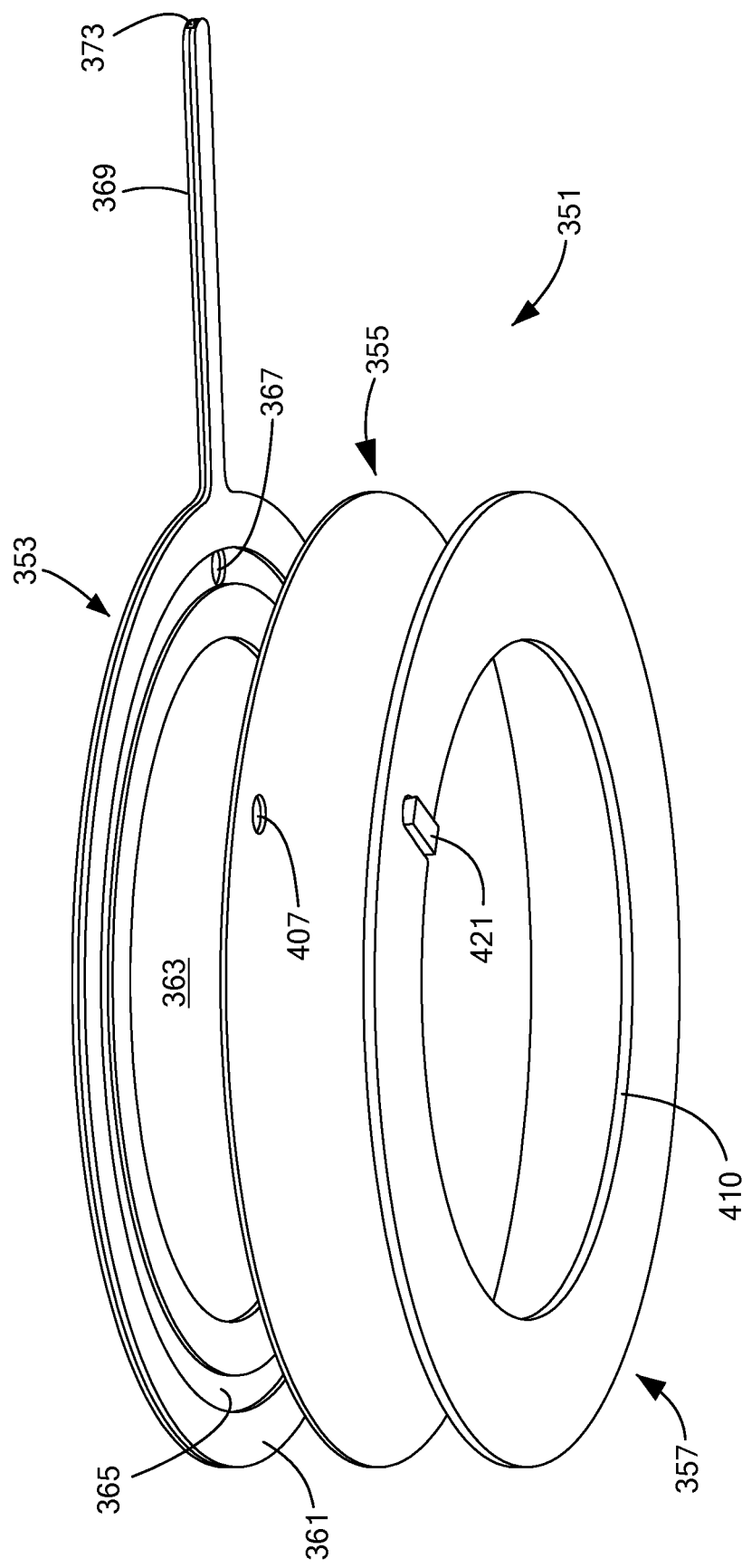

Electrolytic gas generator 311 may also comprise an anode support assembly 331, which may be positioned directly above and in contact with membrane electrode assembly 313. Anode support assembly 331, which is also shown separately in FIGS. 22 and 23, may comprise an anode support gasket 333 and an anode support 335. Anode support gasket 333 may be similar in composition to support gasket 29 of electrolytic gas generator 11 and may have an annular shape that is a generally similar to that of support gasket 29. Anode support 335 may be similar in composition to anode support 15 of electrolytic gas generator 11 but may have a button-shape comprising a lower portion 337 positioned below anode support gasket 333, an upper portion 339 positioned above anode support gasket 333, and an intermediate portion 341 extending through the aperture of support gasket 29. A gasket 343, comprised of a flexible, compliant, non-porous material such as rubber or soft plastic, may peripherally surround, fluidically seal, and electrically insulate anode support 335. Gasket 343 may be dimensioned to have an outer diameter that substantially matches that of membrane electrode assembly 313.

Electrolytic gas generator 311 may also comprise a cathode support 345, which may be positioned directly below and in contact with membrane electrode assembly 313. Cathode support 345 may be similar to cathode support 17 of electrolytic gas generator 11. A support gasket 347, which may be similar to support gasket 31 of electrolytic gas generator 11, may peripherally surround, fluidically seal, and electrically insulate cathode support 345.

Electrolytic gas generator 311 may further comprise an anode current collector assembly 351. Anode current collector assembly 351, which is also shown separately in FIGS. 24, 25, 26(a) and 26(b), may be positioned over and in direct contact with anode support 335 and gasket 343. As will be discussed further below, anode current collector assembly 351 may be constructed to perform three different functions, namely, (1) to conduct current from anode support 335 to an electrically conductive lead conductively mounted (e.g., by soldering) on a component of anode current collector assembly 351, (2) to conduct gas (e.g., O₂) that is generated at anode electrocatalyst layer 325 and passed through anode support 335 along to a length of tubing that may be coupled to anode current collector 351, and (3) to cause the electrolyzing function of electrolytic gas generator 311 to diminish or to stop entirely if the gas pressure on the anode side of membrane electrode assembly 313 becomes too great.

Figure 27C:
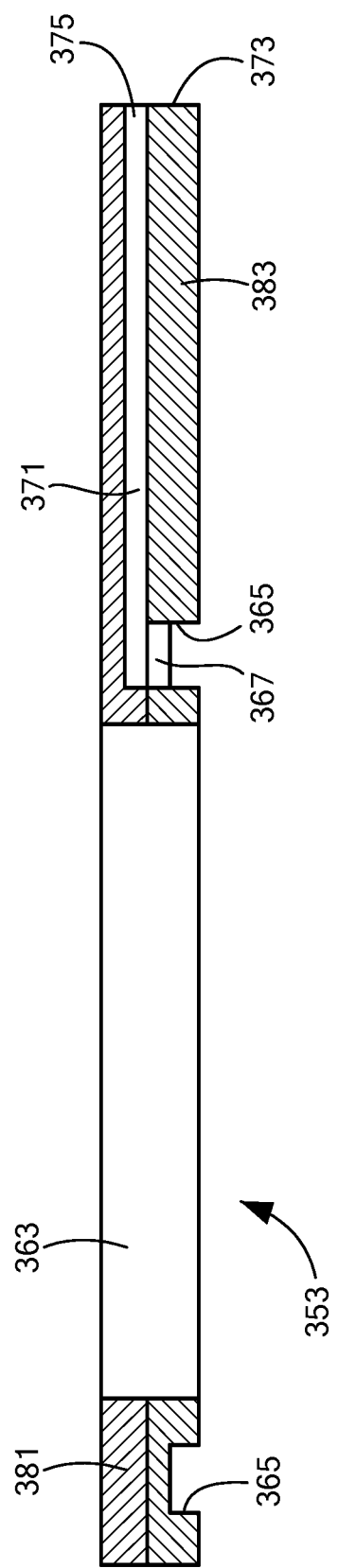

In the present embodiment, anode current collector assembly 351 may comprise an anode current collector 353, a diaphragm 355, and a frame 357, wherein diaphragm 355 is stacked directly between current collector 353 and frame 357. Anode current collector 353, which is also shown separately in FIGS. 27(a) through 27(c), may be shaped to include an annular portion 361 circumscribing an aperture 363. Annular portion 361, which may be dimensioned to have an outer diameter that substantially matches that of gasket 343, may be shaped to include an annular groove 365 provided on a bottom surface of annular portion 361 and may further be shaped to include an inlet 367 disposed within annular groove 365. As will be discussed further below, inlet 367 may be used to receive gas (e.g., O₂) generated at the anode of electrolytic gas generator 311.

Anode current collector 353 may be further shaped to include a first extension 369. First extension 369 may extend radially outwardly from annular portion 361 for a distance. In this manner, a length of fluid-conductive tubing may be coaxially mounted over first extension 369 for purposes to become apparent below. In addition, a conductive lead, which may be electrically coupled to a battery or other suitable current source, may be mounted on first extension 369. In other words, first extension 369 may serve both as a fitting for receiving fluid-conductive tubing and as a contact surface for a conductive lead. If desired, the fluid-conductive tubing and the conductive lead may be mounted on different portions of first extension 369. Although first extension 369 is shown in the present embodiment as having a uniform width along its length, first extension 369 could be shaped like first extension 53 of electrolytic gas generator 11.

A lumen 371 may be provided in anode current collector 353 and may extend continuously from inlet 367 to a distal end 373 of first extension 369, lumen 371 terminating at distal end 373 in an outlet 375. In this manner, as will be discussed further below, a gas, such as oxygen, that is generated at the anode of electrolytic gas generator 311 may enter anode current collector 353 through inlet 367 and may travel through lumen 371, exiting at outlet 375.

Figure 28:
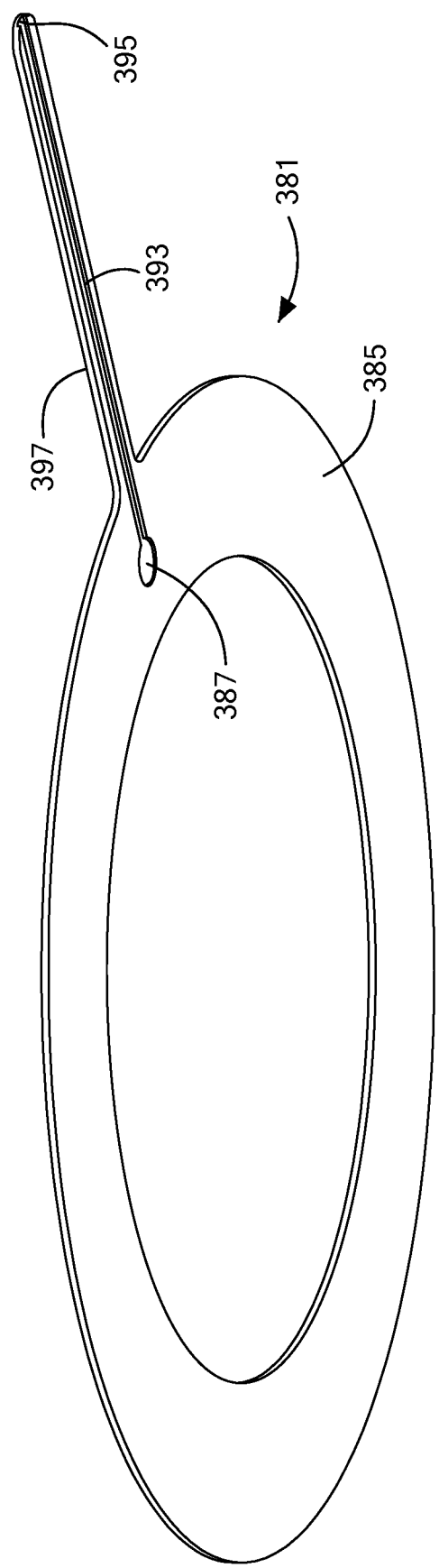
FIG. 28 is a bottom perspective view of the top member of the anode current collector shown in FIG. 24.

In the present embodiment, anode current collector 353 may be formed by the joinder of a top member 381 and a bottom member 383, wherein top member 381 and bottom member 383 have substantially matching profiles. (However, alternatively, anode current collector 353 could be fashioned from a single piece of material.) Top member 381, which is also shown separately in FIG. 28, may be shaped to include a bottom surface 385 having a recess 387. Bottom member 383, which is also shown separately in FIGS. 29(a) and 29(b), may be shaped to include a through hole 391. In this manner, recess 387 of top member 381 and through hole 391 of bottom member 383, which are aligned, may jointly define inlet 367. Bottom surface 385 of top member 381 may be further shaped to include a radial groove or recess 393 extending from recess 387 to a distal end 395 of a tab 397. A top surface 399 of bottom member 383 may be shaped to include a radial groove 401 extending from through hole 391 to a distal end 403 of a tab 405. In this manner, groove 393 of top member 381 and groove 401 of bottom member 383 may jointly define lumen 371. Although, in the present embodiment, top member 381 includes groove 393 and bottom member 383 includes groove 401, lumen 371 could be formed by a groove on only one of top member 381 and bottom member 383.

In the present embodiment, each of top member 381 and bottom member 383 may be a rigid, electrically-conductive plate. Examples of materials suitable for use as top member 381 and/or bottom member 383 may include various conductive and corrosion-resistant metals, such as titanium, niobium, and zirconium. Other examples may include electrically-conductive polymers or polymers in which electrically-conductive particles are dispersed. Where top member 381 and bottom member 383 are formed of titanium or a similarly conductive and corrosion-resistant material, top member 381 and bottom member 383 may be joined by diffusion bonding or by any other suitable technique. In addition, where top member 381 and bottom member 383 are formed of titanium or a similar material, recess 387, through hole 391, and grooves 393 and 401 may be formed by etching (e.g., photoetching, chemical etching) or by any other suitable technique. Preferably, each of top member 381 and bottom member 383 is made of a material that is non-porous and substantially gas-impermeable. In this manner, substantially all gas conducted through anode current collector 353 may enter through inlet 367, may travel through lumen 371, and may exit through outlet 375.

Although both top member 381 and bottom member 383 may be electrically conductive, one could make bottom member 383 from an electrically-conductive material and could make top member 381 from an electrically-non-conductive material. However, in such a case, the conductive lead should be mounted on bottom member 383.

Diaphragm 355 may be an electrically-conductive, flexible, unitary structure in the form of a continuous film or sheet capable of being reversibly deformed (for example, when subjected to gas pressure) from a generally planar state to a bulging or distended state. Diaphragm 355 may be dimensioned so that its periphery substantially matches the outer periphery of annular portion 361 of anode current collector 353.

In the present embodiment, except to the extent specifically provided for below, diaphragm 355 is non-porous. In addition, in the present embodiment, diaphragm 355 is preferably elastic but need not be. According to one embodiment, diaphragm 355 may also be substantially gas-impermeable. Alternatively, according to another embodiment, diaphragm 355 may be gas-permeable. Examples of materials that may be suitable for use as diaphragm 355 include, but are not limited to, non-porous silicones films or sheets with metallic (e.g., silver) or other electrically-conductive particles dispersed therein, Cho-Seal 1215 elastomer (a conductive material made of silver-plated copper film in a silicone binder, a product of Parker Chomerics, Woburn, Mass.), and non-porous, electrically-conductive, liquid-permeable, substantially gas-impermeable membranes of the type disclosed in U.S. Pat. No. 9,595,727 B2, inventors Mittelsteadt et al., which issued Mar. 14, 2017, and which is incorporated herein by reference in its entirety.

More specifically, according to the aforementioned patent (hereinafter "the '727 patent"), such a non-porous, electrically-conductive, liquid-permeable, substantially gas-impermeable membrane may comprise, for example, a solid polymer electrolyte into which electrically-conductive materials are dispersed. Examples of materials suitable for use as the solid polymer electrolyte may include (i) polymer compositions that contain metal salts; (ii) polymeric gels that contain electrolytes; and (iii) ion exchange resins. More specifically, the solid polymer electrolyte may be, for example, a cation exchange ionomer membrane where the cation exchange group may be, but is not limited to, $—SO_3^-$, $—SO_2NH^+$, $—PO_3^{2-}$, or $—CO_2^-$ or may be, for example, an anion exchange ionomer membrane where the anion exchange group may be, but is not limited to, $—NH_2^+$. A preferred material for use as the solid polymer electrolyte may be a perfluorosulfonic acid (PFSA) membrane, such as is manufactured by The Chemours Company FC, LLC (Fayetteville, N.C.) as NAFION™ extrusion cast PFSA polymer membrane. Examples of other materials that may be used in place of NAFION™ PFSA are disclosed in U.S. Pat. No. 7,947,405 B2, inventors Mittelsteadt et al., which issued May 24, 2011, and which is incorporated herein by reference in its entirety.

Examples of materials that may be suitable for use as the dispersed, electrically-conductive materials of the above-described membrane may include high-aspect-ratio, electrically-conductive, non-particulate materials, such as carbon nanotubes, carbon nanofibers, metal nanowires, or combinations thereof. Carbon nanotubes that may be suitable for use in the membrane may have a diameter of about 0.20 nm to about 100 nm, may have a length of about 0.50 μm to about 200 μm, and may have an aspect ratio (i.e., length/diameter) in the range of about 5 to about 1,000,000. Additionally, carbon nanotubes that may be suitable for use in the membrane may be non-functionalized or may include one or more functional groups, such as, but not limited to, $—COOH$, $—PO_4^-$, $—SO_3H$, $—SH$, $—NH_2$, tertiary amines, quaternary amines, $—CHO$, $—OH$, $—NO_2$, and $—PO_3^2$. Moreover, carbon nanotubes that may be suitable for use in the membrane may include single-walled carbon nanotubes, double-walled carbon nanotubes, multi-walled carbon nanotubes, or combinations thereof.

Carbon nanofibers that may be suitable for use in the membrane may be non-functionalized or may include one or more functional groups, such as, but not limited to, $—COOH$, $—PO_4^-$, $—SO_3H$, $—SH$, $—NH_2$, tertiary amines, quaternary amines, $—CHO$, $—OH$, $—NO_2$, and $—PO_3^{2-}$. In addition to including dispersed, non-particulate, electrically-conductive materials or instead of such materials, the membrane may comprise dispersed, electrically-conductive, corrosion-resistant particles, such as, but not limited to, carbon black, metal particles (e.g., niobium particles, platinum particles, titanium particles, or combinations thereof), supported metal particles, or combinations thereof.

The above-described membrane may be prepared by adding the electrically-conductive, corrosion-resistant materials to the ionomer while the ionomer is in suspension form and then drying the suspension.

Diaphragm 355 may comprise a through hole 407 proximate to its periphery. As will be discussed further below, through hole 407 permits the gas generated at the anode, such as oxygen, to pass upwardly through diaphragm 355 so that it may enter inlet 367 of anode current collector 353. To this end, through hole 407 is preferably aligned with annular groove 365 of anode current collector 353.

Figure 30:
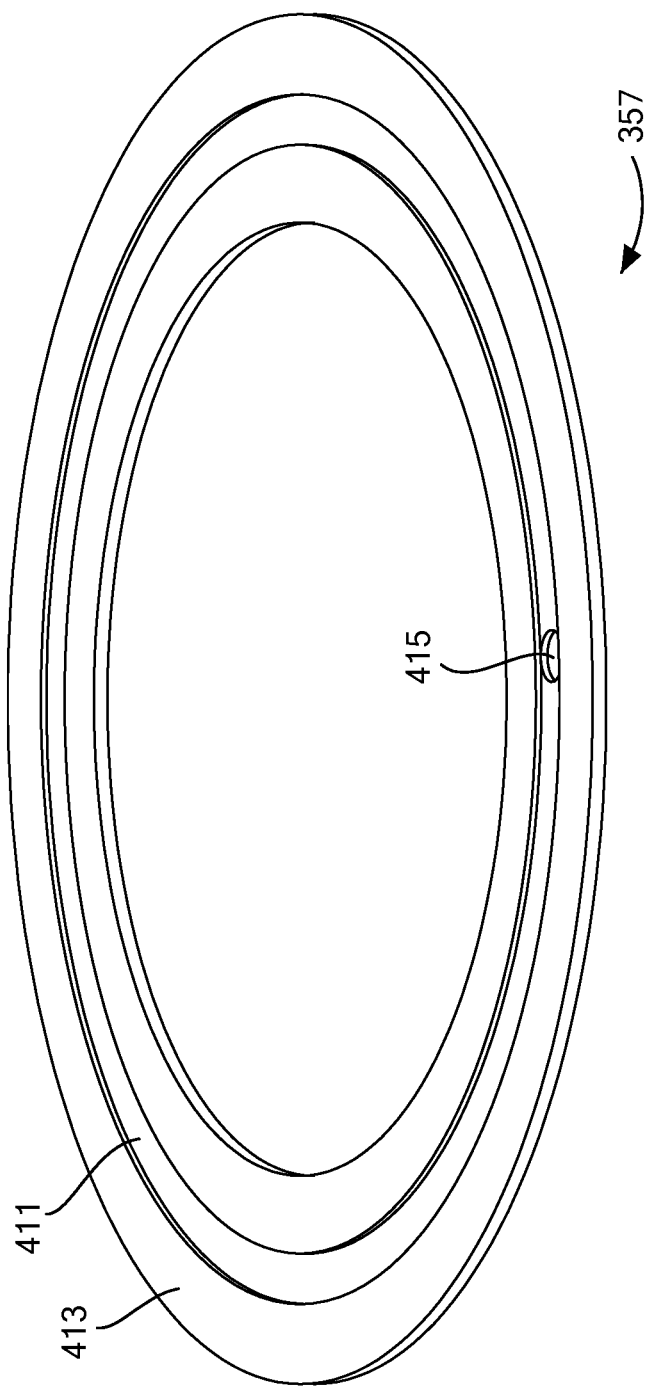
FIG. 30 is a top perspective view of the frame of the anode current collector shown in FIG. 24.

Frame 357, which is also shown separately in FIG. 30, may be an annular structure made of a rigid, non-electrically-conductive material, such as a suitable plastic. Frame 357 preferably has inner and outer diameters that substantially match those of anode current collector 353 and preferably has an aperture 410 that substantially matches the diameter of aperture 363 of anode current collector 353. An annular groove 411 may be formed on a top surface 413 of frame 357, and a through hole 415 may be disposed within annular groove 411. Annular groove 411 of frame 357 is preferably aligned with through hole 407 of diaphragm 355. In this manner, gas generated at the anode may pass upwardly through frame 357 via through hole 415. Then, such gas may pass through diaphragm 355 by traveling around annular groove 411 of frame 357 until reaching through hole 407 of diaphragm 355. After traversing through hole 407, such gas may then travel around annular groove 365 of anode current collector 353 until reaching inlet 367. (Because diaphragm 355 completely covers aperture 410 of frame 357, the only path that gas may take from frame 357 to anode current collector 353 is by traversing through hole 407 of diaphragm 355, which is situated radially outwardly relative to aperture 410.)

A spacer 421, which may be, for example, carbon fiber paper or the like, may be positioned between frame 357 and gasket 343 at a location near (but not covering) through hole 415 of frame 357 to enable gas that is generated at the anode to make its way to through hole 415.

Anode support 335 is preferably dimensioned to extend through aperture 410 of frame 357 so as to make contact with diaphragm 355 when diaphragm is in a planar state. Because diaphragm 355 provides the only electrical connection between anode support 335 and anode current collector 353, diaphragm 355 may be used to regulate the operation of electrolytic gas generator 311. More specifically, when diaphragm 355 is in a planar state, electrolytic gas generator 311 forms a closed electrical circuit and is in an operating (or "on") state for electrolysis. Where water is being electrolyzed, oxygen gas is generated at the anode, and hydrogen gas is generated at the cathode. The thus-generated oxygen gas may then exit electrolytic gas generator 311 through outlet 375. If the rate at which oxygen gas may exit electrolytic gas generator 311 is greater than or approximately equal to the rate at which oxygen gas is generated by electrolytic gas generator 311, very little, if any, oxygen gas may build up between anode support 335 and diaphragm 355, and the upwardly-directed gas pressure exerted on diaphragm 355 may be less than the downwardly-directed mechanical pressure exerted on diaphragm 355. As a result, electrical contact may be maintained between diaphragm 355 and anode support 335, and gas generation may continue.

On the other hand, if the rate at which oxygen gas may exit electrolytic gas generator 311 is less than the rate at which oxygen gas is generated by electrolytic gas generator 311, oxygen gas may build up between anode support 335 and diaphragm 355, and, eventually, the upwardly-directed gas pressure exerted on diaphragm 355 may be greater than the downwardly-directed mechanical pressure exerted on diaphragm 355. As a result, diaphragm 355 may flex or distend away from anode support 335 through aperture 363 of anode current collector 353, thereby breaking or diminishing electrical contact between anode support 335 and diaphragm 355. As a result, electrolytic gas generator 311 may decrease its electrolysis of water or may entirely stop its electrolysis of water. Thereafter, at least some of the oxygen gas that has accumulated between anode support 335 and diaphragm may exit electrolytic gas generator 311 through outlet 375 until the gas pressure between anode support 335 and diaphragm 355 decreases sufficiently for diaphragm 355 to be brought back into contact with anode support 335, thereby permitting electrolysis to resume or to be restored to full capacity.

As can be appreciated, the foregoing scenario may take place in the context of a cell implant system in which the oxygen produced by electrolytic gas generator 311 is conducted by tubing to a closed container holding implanted cells and/or tissue. If the implanted cells and/or tissue cannot consume the oxygen that is delivered thereto at a rate that exceeds or is substantially equal to the rate at which the generated oxygen is delivered or if there is some restriction to flow downstream of outlet 375, oxygen may accumulate in the electrolytic gas generator 311 as described above. If the amount of oxygen that accumulates within electrolytic gas generator 311 is sufficient to create a pressure that exceeds a predetermined threshold, electrolytic gas generator 311 stops generating oxygen or reduces oxygen output. In this manner, electrolytic gas generator 311 may be regarded as being self-regulating. As can be appreciated, such a self-regulating electrolytic gas generator is advantageous for at least the reason that it does not require external sensors or feedback mechanisms. Further information regarding this type of self-regulating operation may be found in U.S. Patent Application Publication No. US 2018/0135948 A1, inventors Stone et al., published May 17, 2018, which is incorporated herein by reference in its entirety.

Electrolytic gas generator 311 may further comprise a resiliently-compressible member 431. Resiliently-compressible member 431 may be a structure designed to permit diaphragm 355 to deform or to distend upwardly away from and out of contact with anode support 335 when the gas pressure between diaphragm 355 and anode support 335 exceeds a certain threshold gas pressure and to cause or to bias diaphragm 355 to flatten or to deflate downwardly back into contact with anode support 335 when the gas pressure between diaphragm 355 and anode support 335 falls below a certain threshold gas pressure. The threshold gas pressure at which resiliently-compressible member 431 may permit diaphragm 355 to flex away from anode support 335 and the threshold gas pressure at which resiliently-compressible member 431 may cause diaphragm 355 to flex back into contact with anode support 335 may be the same or may be different. In some cases, it may be advantageous for the threshold gas pressure at which resiliently-compressible member 431 allows diaphragm 355 to flex away from anode support 335 to be significantly greater than the threshold gas pressure at which resiliently-compressible member 431 forces diaphragm 355 to flex back into contact with anode support 335. Consequently, in such a case, once the operation of electrolytic gas generator 311 has stopped, it will not resume until the gas pressure between diaphragm 355 and anode support 335 has dropped significantly. In this manner, electrolytic gas generator 311 may be prevented from undesirably stuttering back and forth between its operating and off states.

In the present embodiment, resiliently-compressible member 431 may comprise a block or disc of an electrically insulating material, such as foam. Such foam may be a closed-cell foam or an open-cell foam. Examples of suitable foams may include, but are not limited to, polyurethane foams and silicone rubber foams, such as an open-cell silicone rubber foam. Although, in the present embodiment, resiliently-compressible member 431 may be a block of foam, resiliently-compressible member 431 is not limited thereto and may be any type of resiliently-compressible structure, such as, but not limited to, a coil spring, a Belleville spring, an enclosed gas pocket, a gas pocket with an externally referenceable gas filling port, or combinations thereof.

Electrolytic gas generator 311 may further comprise a sealing spacer 433. Sealing spacer 433, which may be a flexible member having a recessed central portion, may be disposed between resiliently-compressible member 431 and anode current collector 353. Sealing spacer 433 may be used to compensate for any additional space that may be needed between anode current collector 353 and the housing. This may be the case, for instance, if resiliently-compressible member 431 is thicker than one expected it to be and one needs to make extra space in the housing.

Electrolytic gas generator 311 may further comprise a cathode current collector 441. Cathode current collector 441, which is shown separately in FIGS. 31(a) and 31(b), may be similar in many respects to cathode current collector 91 of electrolytic gas generator 11. One difference between cathode current collector 441 and cathode current collector 91 may be that, whereas cathode current collector 91 may comprise a first extension 103 having a proximal portion 105 of comparatively greater width and a distal portion 107 of comparatively lesser width, cathode current collector 441 may comprise a first extension 443 having a substantially uniform width. Another difference between cathode current collector 441 and cathode current collector 91 may be that, whereas cathode current collector 91 may have a second extension 115, cathode current collector 441 may omit a second extension. Still another difference between cathode current collector 441 and cathode current collector 91 may be that, whereas cathode current collector 91 may have a central through hole 99 of greater diameter and a large number of pores 100 of smaller diameter, cathode current collector 441 may comprise a central through hole 445 and a small number of pores 447, wherein through hole 445 and pores 447 may have substantially the same diameter.

Analogously to cathode current collector 91, cathode current collector 441 may have an outlet 449 at a distal end of extension 443 and may have a lumen 450 extending from through hole 445 to outlet 449. Cathode current collector 441 may function analogously to cathode current collector 91. To this end, cathode current collector 441 is preferably made of a material that is sufficiently non-porous and gas-impermeable such that substantially all gas conducted through cathode current collector 441 may enter through inlet 445, may travel through lumen 450, and may exit through outlet 449.

Electrolytic gas generator 311 may further comprise a housing base 451 and a housing cover 453, housing base 451 and housing cover 453 jointly defining a housing that may be used to hold many of the other components of electrolytic gas generator 311. Housing base 451, which may be a unitary structure made of a rigid, durable, electrically-non-conductive material, may be shaped to include a bottom wall 455, a side wall 457, and an open top. Bottom wall 455 may be shaped to include one or more openings 459 designed to allow a fluid, such as liquid water, to enter into the interior of housing. Side wall 457 may be shaped to include a first opening 461 designed to allow extensions 369 and 443 to pass therethrough. Housing cover 453, which may be a unitary structure made of a rigid, durable, electrically-non-conductive material, may be shaped to include a top portion 465 and a bottom portion 467. A plurality of through holes 468 may extend through top portion 465 and bottom portion 467. Through holes 468 may be used to allow the outside (i.e., relative to the housing) ambient pressure to be used as a reference pressure for electrolytic gas generator 311. In other words, if electrolytic gas generator 311 is implanted in a body, the body's pressure will be used as the reference pressure pushing against diaphragm 355. Top portion 465 may be shaped to substantially match the footprint of housing base 451 and may have a bottom surface designed to sit directly on top of the top surface of side wall 457. Bottom portion 467 may be shaped to have a footprint that substantially matches the inner diameter of housing base 451 and may be used to help compress the components stacked within the housing. In this manner, housing base 451 and housing cover 453 not only function to provide a housing for the components of electrolytic gas generator 311 but also function as endplates.

Electrolytic gas generator 311 may further comprise water-control membranes 481 and 482. Water-control membranes 481 and 482 may be positioned between cathode current collector assembly 441 and bottom wall 455 of housing base 451. In the present embodiment, water-control membrane 481 may be a biocompatible membrane that prevents biofouling in order to promote a stable and consistent water vapor source. An example of a material that may be suitable for use as water-control membrane 481 is expanded PTFE with at least some of the pores being 3 µm or greater in diameter and a preferred thickness range of 30-50 µm. Water-control membrane 482 may be in the form of a vapor transport membrane. Examples of materials suitable for use as water-control membrane 482 may include, but are not limited to, ZITEX® porous polytetrafluoroethylene, GORE-TEX® expanded polytetrafluoroethylene, silicone rubber, PTFE, and TEFLON® polytetrafluoroethylene.

Electrolytic gas generator 311 may be used in the fashion described above.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. An electrolytic gas generator for electrolyzing a reactant to generate at least a first gas, the electrolytic gas generator comprising:
   (a) a polymer electrolyte membrane, the polymer electrolyte membrane having opposing first and second faces;
   (b) a first electrode, the first electrode being electrically coupled to the first face of the polymer electrolyte membrane;
   (c) a second electrode, the second electrode being electrically coupled to the second face of the polymer electrolyte membrane;
   (d) a first current collector, the first current collector being electrically coupled to the first electrode, wherein the first current collector comprises a first electrically-conductive extension and wherein the first current collector further comprises a gas conduit extending laterally for porting laterally the first gas generated at the first electrode;
   (e) a second current collector, the second current collector being electrically coupled to the second electrode;
   (f) a current source;
   (g) a first conductive lead, the first conductive lead electrically coupling the first current collector to the current source, the first conductive lead comprising a first end secured to the first electrically-conductive extension; and
   (h) a second conductive lead, the second conductive lead electrically coupling the second current collector to the current source.

2. The electrolytic gas generator as claimed in claim 1 wherein the electrolytic gas generator is a water electrolyzer.

3. The electrolytic gas generator as claimed in claim 1 wherein at least a portion of the gas conduit passes through at least a portion of the first electrically-conductive extension.

4. The electrolytic gas generator as claimed in claim 3 wherein the first electrically-conductive extension terminates at a distal end thereof and wherein the gas conduit passes entirely through the first electrically-conductive extension to said distal end thereof to laterally port gas through the distal end of the first electrically-conductive extension.

5. The electrolytic gas generator as claimed in claim 1 wherein the first current collector comprises a top member and a bottom member, the top member and the bottom member being bonded to one another and jointly defining the gas conduit.

6. The electrolytic gas generator as claimed in claim 1 wherein the first current collector comprises a top member and a bottom member, the top member and the bottom member being bonded to one another and jointly defining the gas conduit and the first electrically-conductive extension.

7. The electrolytic gas generator as claimed in claim 5 wherein the gas conduit is formed by one or more etchings on at least one of the top member and the bottom member.

8. The electrolytic gas generator as claimed in claim 7 wherein the gas conduit is formed by one or more etchings on both the top member and the bottom member.

9. The electrolytic gas generator as claimed in claim 7 wherein the gas conduit is formed by a through hole on the bottom member and an elongated recess on the top member, the elongated recess having a first end aligned with the through hole of the bottom member and a second end at the periphery of the top member.

10. The electrolytic gas generator as claimed in claim 5 wherein both the top member and the bottom member are electrically conductive.

11. The electrolytic gas generator as claimed in claim 5 wherein the bottom member is electrically conductive and the top member is electrically-non-conductive.

12. The electrolytic gas generator as claimed in claim 1 wherein the first current collector further comprises a second electrically-conductive extension for use in mounting a conductive lead.

13. The electrolytic gas generator as claimed in claim 12 wherein the first electrically-conductive extension and the second electrically-conductive extension are spaced apart from one another by approximately 180 degrees.

14. The electrolytic gas generator as claimed in claim 1 wherein the first electrically-conductive extension has a proximal portion of comparatively greater width and a distal portion of comparatively lesser width.

15. The electrolytic gas generator as claimed in claim 1 wherein the first electrically-conductive extension has a substantially uniform width.

16. The electrolytic gas generator as claimed in claim 1 wherein the second current collector comprises a first electrically-conductive extension for use in mounting a conductive lead and wherein the second current collector further comprises a gas conduit for porting laterally gas generated at the second electrode.

17. The electrolytic gas generator as claimed in claim 16 wherein at least a portion of the gas conduit of the second current collector passes through at least a portion of the first electrically-conductive extension of the second current collector.

18. The electrolytic gas generator as claimed in claim 16 wherein the second current collector comprises a top member and a bottom member, the top member and the bottom member being bonded to one another and jointly defining the gas conduit of the second current collector.

19. The electrolytic gas generator as claimed in claim 16 wherein the second current collector comprises a top member and a bottom member, the top member and the bottom member being bonded to one another and jointly defining the gas conduit of the second current collector and the first electrically-conductive extension of the second current collector.

20. The electrolytic gas generator as claimed in claim 1 further comprising a diaphragm interposed between the first electrode and the first current collector, the diaphragm being electrically-conductive and being reversibly deformable between a first state in which the diaphragm electrically couples the first current collector to the first electrode and a second state in which the first current collector is at least partially disconnected from the first electrode.

21. The electrolytic gas generator as claimed in claim 20 wherein the diaphragm has an aperture for passage therethrough of gas generated at the first electrode, the aperture being positioned proximate to a periphery of the diaphragm in a location that does not electrically contact the first electrode.

22. An electrolytic gas generator for electrolyzing a reactant to generate at least a first gas, the electrolytic gas generator comprising:
(a) a polymer electrolyte membrane, the polymer electrolyte membrane having opposing first and second faces;
(b) a first electrode, the first electrode being electrically coupled to the first face of the polymer electrolyte membrane;
(c) a second electrode, the second electrode being electrically coupled to the second face of the polymer electrolyte membrane;
(d) a first current collector assembly, the first current collector assembly comprising
a first current collector, wherein the first current collector comprises a first electrically-conductive extension and wherein the first current collector further comprises a gas conduit for porting laterally the first gas generated at the first electrode,
a frame, the frame being non-electrically-conductive,
a diaphragm, the diaphragm being secured between the first current collector and the frame, the diaphragm being electrically-conductive and being reversibly deformable between a first state in which the first current collector is electrically coupled to the first electrode and a second state in which the first current collector is at least partially electrically disconnected from the first electrode;
(e) a second current collector, the second current collector being electrically-conductive and being electrically coupled to the second electrode;
(f) a current source;
(g) a first conductive lead, the first conductive lead electrically coupling the first current collector to the current source, the first conductive lead comprising a first end secured to the first electrically-conductive extension; and
(h) a second conductive lead, the second conductive lead electrically coupling the second current collector to the current source.

23. The electrolytic gas generator as claimed in claim 22 wherein the diaphragm has an aperture for passage therethrough of gas generated at the first electrode, the aperture being positioned proximate to a periphery of the diaphragm in a location that does not electrically contact the first electrode.

24. The electrolytic gas generator as claimed in claim 23 wherein the first current collector further comprises an annular portion and wherein the first electrically-conductive extension extends radially outwardly from the annular portion.

25. The electrolytic gas generator as claimed in claim 24 wherein the annular portion of the first current collector comprises an annular recess of a bottom surface thereof, wherein an inlet to the gas conduit is positioned within the annular recess, and wherein the aperture of the diaphragm is aligned with the annular recess of the first current collector.

26. The electrolytic gas generator as claimed in claim 25 wherein the frame is annular, wherein the frame comprises an annular recess on a top surface thereof, wherein the frame has an aperture, wherein the aperture of the frame is positioned within the annular recess of the frame, and wherein the annular recess of the frame is aligned with the aperture of the diaphragm.

27. The electrolytic gas generator as claimed in claim 26 wherein the first current collector comprises a top member and a bottom member, the top member and the bottom member being bonded to one another and jointly defining the gas conduit.

28. The electrolytic gas generator as claimed in claim 26 wherein the first current collector comprises a top member and a bottom member, the top member and the bottom member being bonded to one another and jointly defining the gas conduit and the first electrically-conductive extension.

29. The electrolytic gas generator as claimed in claim 22 further comprising a resiliently-compressible member engaged with the first current collector to bias the first current collector towards the first state.

30. A current collector for use in an electrolytic gas generator, the current collector comprising:
(a) a body, the body being electrically conductive; and
(b) an extension, the extension extending laterally from the body and terminating at a distal end thereof, the extension comprising an electrically-conductive surface electrically coupled to the body;
(c) wherein the body and the extension jointly define a gas conduit, the gas conduit having a first end in the body and extending entirely through the extension to the distal end thereof to laterally port gas through the distal end of the extension.

31. The current collector as claimed in claim 30 wherein the body is disk-shaped and wherein the extension extends radially from the body.

32. The current collector as claimed in claim 30 wherein the first end of the gas conduit terminates in a through hole in the body.

33. The current collector as claimed in claim 30 wherein the first end of the gas conduit terminates in an opening at a bottom surface of the body.

34. The current collector as claimed in claim 30 wherein the body is annular and wherein the extension extends radially from the body.

35. The current collector as claimed in claim 30 wherein the body and the extension are formed by joining a top member and a bottom member, the top member and the bottom member being bonded to one another and jointly defining the gas conduit.

36. The current collector as claimed in claim 30 wherein the body and the extension are formed by joining a top member and a bottom member, the top member and the bottom member being bonded to one another and jointly defining the gas conduit and the extension.

37. The current collector as claimed in claim 36 wherein the gas conduit is formed by one or more etchings on at least one of the top member and the bottom member.

38. The current collector as claimed in claim 37 wherein the gas conduit is formed by one or more etchings on both the top member and the bottom member.

39. The current collector as claimed in claim 30 wherein the body has a top surface and a bottom surface and wherein the body further comprises one or more pores extending from the top surface to the bottom surface.

40. The current collector as claimed in claim 33 wherein the body further has a top surface and wherein the first end of the gas conduit is a through hole extending entirely through the body from the top surface to the bottom surface.

41. The electrolytic gas generator as claimed in claim 1 wherein the first current collector further comprises a body and wherein the first electrically-conductive extension extends laterally outwardly from the body.

42. The electrolytic gas generator as claimed in claim 41 wherein the body comprises a disk portion and wherein the first electrically-conductive extension extends radially outwardly from the disk portion.

43. The electrolytic gas generator as claimed in claim 41 wherein the body is annular and wherein the extension extends radially outwardly from the body.

* * * * *